(12) United States Patent
Fox et al.

(10) Patent No.: US 9,528,919 B2
(45) Date of Patent: Dec. 27, 2016

(54) SAMPLE PREPARATION DEVICE AND ASSOCIATED METHOD

(75) Inventors: William Alan Fox, Burlington, NC (US); Ryan Carl Williams, Durham, NC (US); Brian Reuben Langhoff, Julian, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 982 days.

(21) Appl. No.: 13/266,351

(22) PCT Filed: Apr. 27, 2010

(86) PCT No.: PCT/US2010/032510
§ 371 (c)(1),
(2), (4) Date: Jan. 10, 2012

(87) PCT Pub. No.: WO2010/126866
PCT Pub. Date: Nov. 4, 2010

(65) Prior Publication Data
US 2012/0100557 A1 Apr. 26, 2012

Related U.S. Application Data

(60) Provisional application No. 61/172,809, filed on Apr. 27, 2009.

(51) Int. Cl.
*G01N 1/36* (2006.01)
*G01N 1/31* (2006.01)

(52) U.S. Cl.
CPC .................................. *G01N 1/312* (2013.01)

(58) Field of Classification Search
CPC ..................................................... G01N 1/312

USPC .................................. 422/50; 435/7.1, 287.2
See application file for complete search history.

(56) References Cited

U.S. PATENT DOCUMENTS

| | | | |
|---|---|---|---|
| 6,183,693 B1 | 2/2001 | Bogen et al. | |
| 6,403,931 B1 | 6/2002 | Showalter et al. | |
| 2003/0017075 A1* | 1/2003 | Angros | 422/63 |
| 2003/0082605 A1 | 5/2003 | Hodge | |

(Continued)

OTHER PUBLICATIONS

International Search Report and Written Opinion for International Application No. PCT/US2010/032510, mailed Aug. 4, 2010.

*Primary Examiner* — Mark Shibuya
*Assistant Examiner* — Pensee Do
(74) *Attorney, Agent, or Firm* — Lerner, David, Littenberg, Krumholz & Mentlik, LLP

(57) ABSTRACT

A sample preparation device and associated method is provided for preparing samples according to an assay protocol. A cell deposition module deposits a sample on each a plurality of assay devices supported by a support device. An epitope retrieval module deposits a reagent on each of the samples. Each of the samples is brought to a selected temperature. A heating device, corresponding to each of the assay devices, directly interacts with the corresponding assay device may be used to heat each assay device to the selected temperature, in conjunction with the epitope retrieval module depositing the reagent on each of the samples. A staining module deposits a staining reagent on each of the samples, and removes excess staining reagent. The staining, epitope retrieval, and cell deposition modules cooperate with the support device and heating devices to form a unitary sample preparation device.

9 Claims, 24 Drawing Sheets

(56) References Cited

U.S. PATENT DOCUMENTS

| | | | |
|---|---|---|---|
| 2003/0203493 A1* | 10/2003 | Lemme et al. | 436/46 |
| 2004/0009098 A1 | 1/2004 | Torre-Bueno | |
| 2004/0197230 A1 | 10/2004 | Lemme et al. | |
| 2005/0042768 A1 | 2/2005 | Fredrick | |
| 2006/0190185 A1 | 8/2006 | Ford et al. | |
| 2008/0113440 A1 | 5/2008 | Gurney et al. | |
| 2008/0213804 A1* | 9/2008 | Erickson et al. | 435/7.23 |
| 2008/0231804 A1 | 9/2008 | Gagne et al. | |
| 2009/0275076 A1* | 11/2009 | Knesel et al. | 435/40.51 |

* cited by examiner

SAMPLE PREPARATION DEVICE AND ASSOCIATED METHOD

CROSS REFERENCE TO RELATED APPLICATIONS

This application is a national stage application filed under 35 U.S.C. 371 of International Application No. PCT/2010/0325210, filed Apr. 27, 2010, which claims priority from U.S. Provisional Application No. 61/172,809, filed Apr. 27, 2009, each of which is incorporated herein in its entirety.

BACKGROUND

Field of the Invention

The present invention relates to automated sample preparation and, more particularly, to an automated device and associated method for preparing cytological samples for analysis.

Description of Related Art

Immunochemistry involves the study of reactions and components of the immune system for the purpose of further diagnosing conditions that may be occurring in a subject. Cytology is a branch of biology dealing with the microscopic study of cells for purposes of medically diagnosing any abnormality, malignancy, or disease in a subject from where a specimen has been taken. Cytological techniques have achieved some acceptance at least partially because the collection of cell samples for subsequent analysis may generally be less invasive than other surgical pathological procedures, such as biopsies. For example, the cell samples used for cytological analysis can be obtained by scraping or swabbing an area of interest. Cell samples may also be obtained from an appropriate area of interest in the body of a subject by using a needle to aspirate bodily fluids from a subject. Additionally, histology is involves the study of tissue to support further medical diagnosis.

The purpose of preparing a sample, in particular a cytological sample, is to extract a desired component from the specimen so that an analysis can be performed. For example, whole blood comprises a variety of immiscible components such as red cells, white cells, platelets, etc. Often the analysis must be performed on the plasma. Further, once the desired component is isolated, it must be placed in a form suitable for subsequent analysis. In some instances, the extracted portion itself may require additional processing to render it capable of being analyzed, depending, for example, on the type of analysis to be performed. Conventional preprocessing techniques may include, for example, staining, a monolayer preparation process for preventing deformations of red blood cells, and a process for the homogeneous distribution of dry particles on a specimen slide in a unilayered, planar distribution.

Cells or tissues that have been collected from a subject may be appropriately prepared on an assay device, on which an analysis is more readily conducted and any apparent condition/pathology possibly diagnosed. Microscope slides such as, for example, deep-well slides, may be used as assay devices. Generally, it may be desirable that the cell or tissue sample be applied to and disposed substantially evenly and consistently across the surface of the assay device, particularly in a thin monolayer of cells, where the analysis (i.e., visual examination) is to be performed. However, it may be difficult to assess cell and tissue preparations (samples) on an assay device by visual examination where such preparations have not been subjected to certain further treatment. For example, lack of contrast between the individual cells or between the individual parts of cells may obscure a visual examination of the sample. In order to improve the contrast, the cell or tissue specimen applied to the assay device may be further treated with reagents in a staining process. Staining reagents are specifically chosen, depending upon the types of cells or tissues being examined, such that their absorbance is distinctively different across the various structures that are or could be present in the specimen. Staining improves the contrast between the different cell structures allowing for improved diagnosis based on a visual examination thereof.

Preparation of clinical cytological specimens in an assay for subsequent analysis requires a sequence of steps that can be exceedingly time consuming if practiced manually. Immunocytochemistry, for example, is a particular type of cytological assay preparation where protein markers are used to detect particular chemical components of cells. In immunocytochemistry, an antibody is selected such that it desirably becomes coupled to a substance of interest allowing the presence of the substance to become more readily detectable upon visual examination. Immunocytochemistry assays generally require three serial procedures. First, a sample of the specimen is disposed on an assay device, such as a slide using a cell deposition procedure. Once the sample is associated with the assay device, an epitope retrieval may be performed. Typically, epitope retrieval requires the addition of a reagent to the sample and, optionally, is followed by a heating step to raise the temperature of the sample for a prescribed amount of time. The sample may then be stained by the addition of an appropriate reagent to, and subsequent removal of any excess reagent from, the assay device (slide) being prepared. In some instances, a cover piece may be placed on the assay device in order to cover the prepared sample.

Each of the serial procedures for preparing the sample is desirably executed in a precise, consistent, repeatable and accurate manner in order to facilitate diagnosis based on the visual examination. Furthermore, emphasis on improving and economizing health care has created an increased demand on sample analysis procedures to assist with diagnosis and to provide information associated with treatment recommendations. These demands require that the sample analysis be accurate and, in many instances, be performed quickly.

As such, there exists a need for more efficient cytological sample preparation systems for improving the consistency, repeatability, and accuracy of sample preparation and analysis. In addition, manual intervention and/or manual processing in the sample preparation process may increase the likelihood that a sample will become contaminated. Any further analysis of such a contaminated sample may lead to an improper medical diagnosis. Manual intervention/manual processing may also increase the risk that the operator can become infected with any sample-borne virus or disease that may be present in the specimen. There exists a further need for more efficient cytological sample preparation systems that eliminate, reduce, or otherwise minimize, where possible, manual intervention and/or manual processing during sample preparation, such as, for example, through automation. Such a cytological sample preparation system should desirably be, for example, relatively easy to use and adaptable for processing a varying numbers of samples.

BRIEF SUMMARY OF THE INVENTION

The above and other needs are met by the present invention which, in one aspect, provides a sample preparation device for preparing a sample according to an assay protocol. Such a sample preparation device comprises a support device configured to support a plurality of assay devices. A cell deposition module is operably engaged with the support device and is configured to deposit a sample on each of the plurality of assay devices supported by the support device. An epitope retrieval module is operably engaged with the support device and the cell deposition module, and is configured to deposit at least one reagent on each of the samples according to the assay protocol. Each sample is brought to a selected temperature using a heating source. According to an embodiment of the invention, the sample is a cytological sample. Further to this embodiment, the assay protocol may be an immunocytochemistry assay protocol.

The reagent applied to the samples may be sufficient to bring the samples to the selected temperature. For example, in circumstances where it is necessary to raise the temperature of the sample to the selected temperature, then the reagent may be provided with or will have the necessary internal energy for doing so. Alternatively, at least one heating device that corresponds to and is operably engaged with the support device is configured to attain compliance with the support device so as to heat the plurality of assay devices to the selected temperature. Instead, a heating device corresponding to each of the plurality of assay devices may be provided, where the heating device is operably engaged with the support device and is configured to attain compliance with the corresponding assay device so as to heat each of the plurality of assay devices to a selected temperature. Nonetheless, these operations are performed in conjunction with the epitope retrieval module depositing the at least one reagent on each of the samples, according to the assay protocol.

A staining module is operably engaged with the support device, the cell deposition module, and the epitope retrieval module. The staining module is configured to deposit a staining reagent on each of the samples according to the assay protocol, and to remove excess staining reagent therefrom upon staining of the samples. The staining module, the epitope retrieval module, and the cell deposition module cooperate with the support device and any heating devices, which optionally may be configured in the sample preparation device, to form a unitary sample preparation device for preparing the sample without movement of the assay devices via the support device.

Another aspect of the present invention provides a method of preparing a sample according to an assay protocol, using a unitary sample preparation device. Such a method comprises supporting a plurality of assay devices with a support device, and depositing a sample on each of the plurality of assay devices supported by the support device in a cell deposition module operably engaged therewith. At least one reagent is deposited on each of the samples, according to the assay protocol, in an epitope retrieval module operably engaged with the cell deposition module and the support device. The method also comprises the step of bringing each of the samples to a selected temperature. According to an embodiment of the invention, the sample is a cytological sample.

Each of the plurality of assay devices may be heated to reach the selected temperature. In certain embodiments, a heating device may correspond to each support device, which is particularly useful when the support device includes a carriage assembly, while, in other embodiments, a heating device may correspond to each of the plurality of assay devices, wherein each heating device is operably engaged with the support device and is configured to directly interact with the corresponding assay device, in conjunction with depositing the at least one reagent on each of the samples, according to the assay protocol. A staining reagent is deposited on each of the samples, according to the assay protocol, and excess staining reagent removed therefrom upon staining of the samples, in a staining module operably engaged with the epitope retrieval module, the cell deposition module, and the support device. The staining module, the epitope retrieval module, and the cell deposition module cooperate with the support device and the any heating devices, which optionally may be configured in the sample preparation device, for preparing the sample without movement of the assay devices via the support device.

Embodiments of the present invention may thus provide improvements over conventional sample preparation systems by combining a staining module, an epitope retrieval module, a cell deposition module, a support device and, any individual heating devices, which optionally may be included in the sample preparation device, in a unitary apparatus capable of preparing the sample without movement of the assay devices via the support device. As such, the samples are not required to be moved or otherwise excessively handled during the preparation procedure and, since major sample preparation procedures are combined into a single automated process, increased operational efficiencies may be realized. Further, possible advantages of aspects of the present invention may include a reduction in the amount of time needed to prepare each sample and a higher sample preparation throughput rate, as compared to non-unitary systems; decreased human contact and/or manual handling in the sample preparation process that may result in lower processing costs associated with each prepared sample, less risk of sample contamination, and less risk of human exposure to potential sample-borne viruses and the like that may be present in a specimen. In addition, due to efficiencies that may be realized from aspects of the present invention, a smaller sample may be collected for a given analysis, the precision of the analytical process may be improved due to increased uniformity in the sample preparation, training and operational costs may decrease as a result of the unitary and automated nature of the device and process, and the unitary nature of the device may reduce the footprint of the components needed to prepare the sample.

As such, aspects of the present invention may provide these and other advantages as further disclosed herein.

BRIEF DESCRIPTION OF THE SEVERAL VIEWS OF THE DRAWINGS

Figure 1:
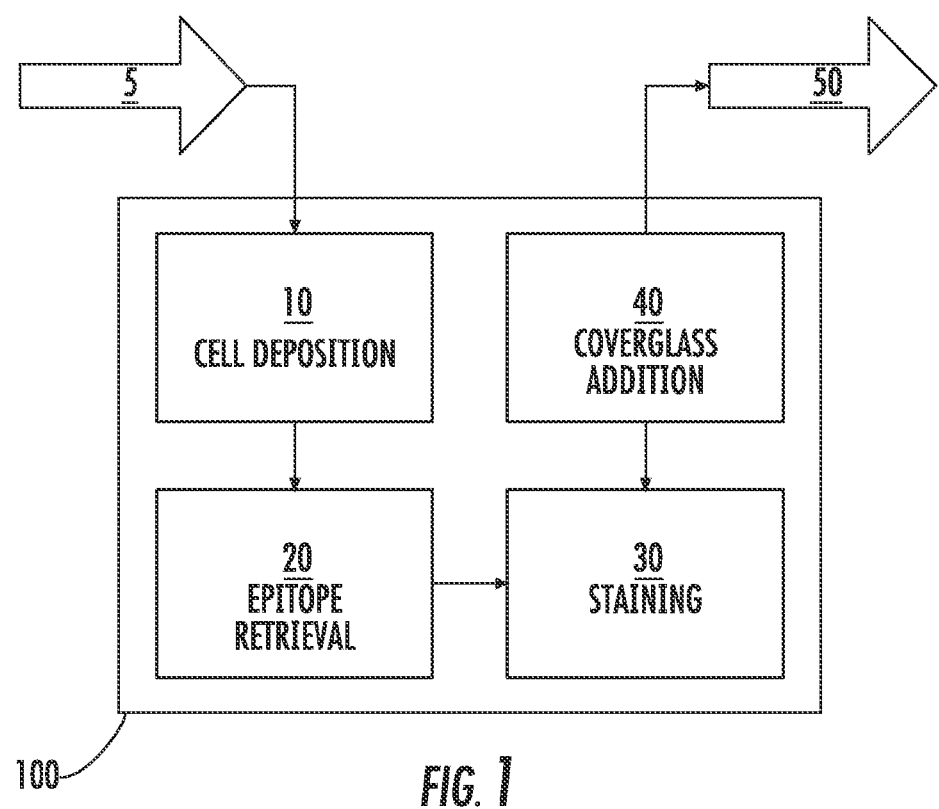
Figure 2:
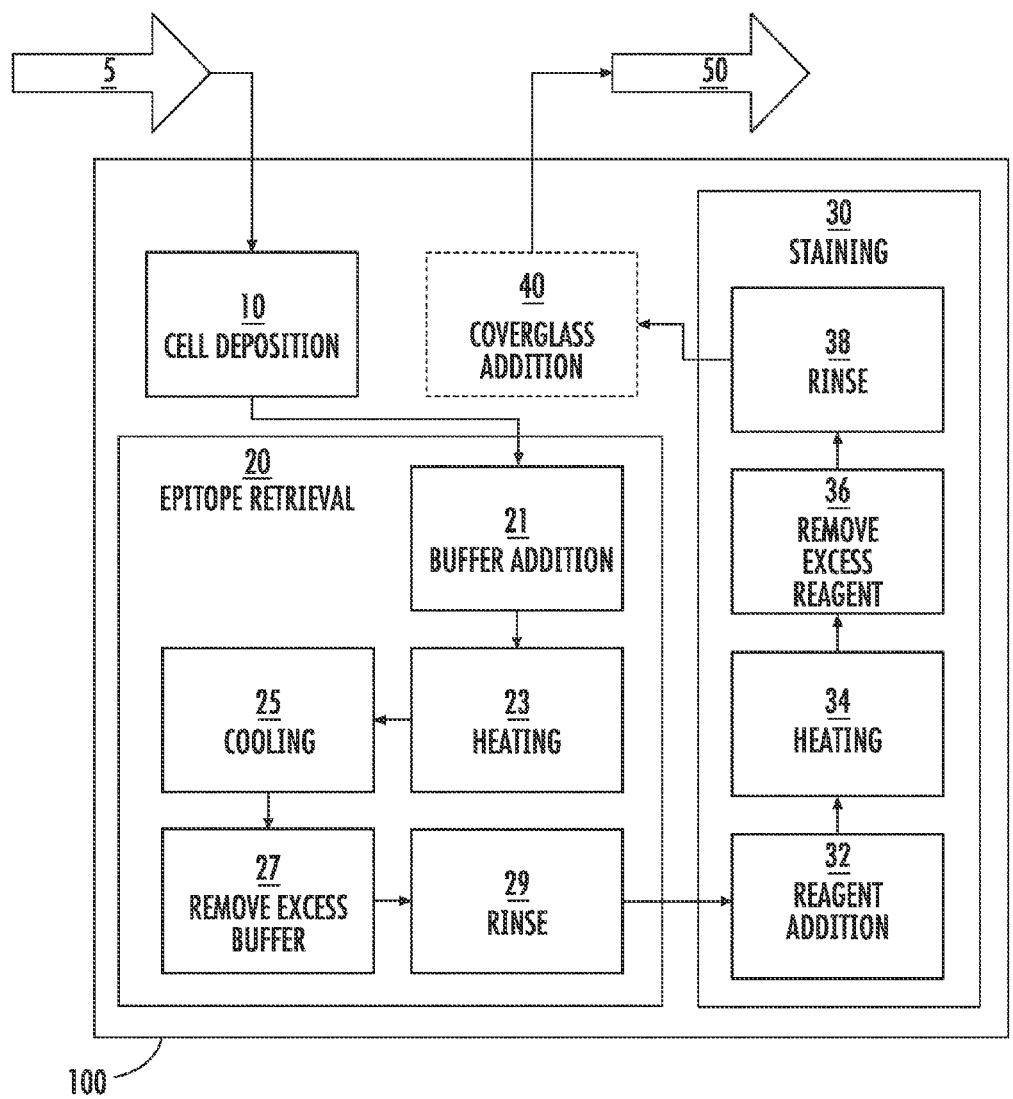
Figure 3:
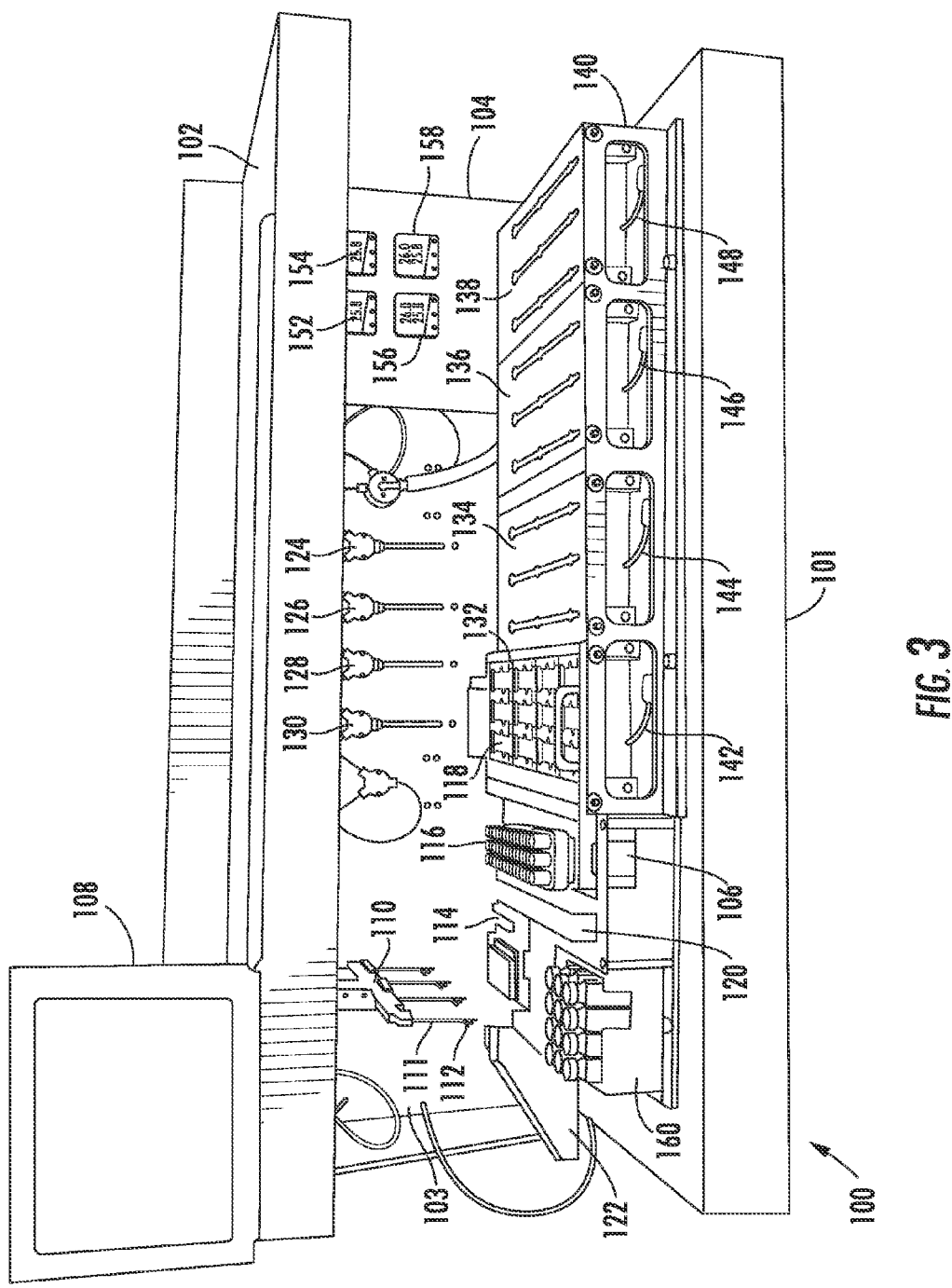
Figure 4:
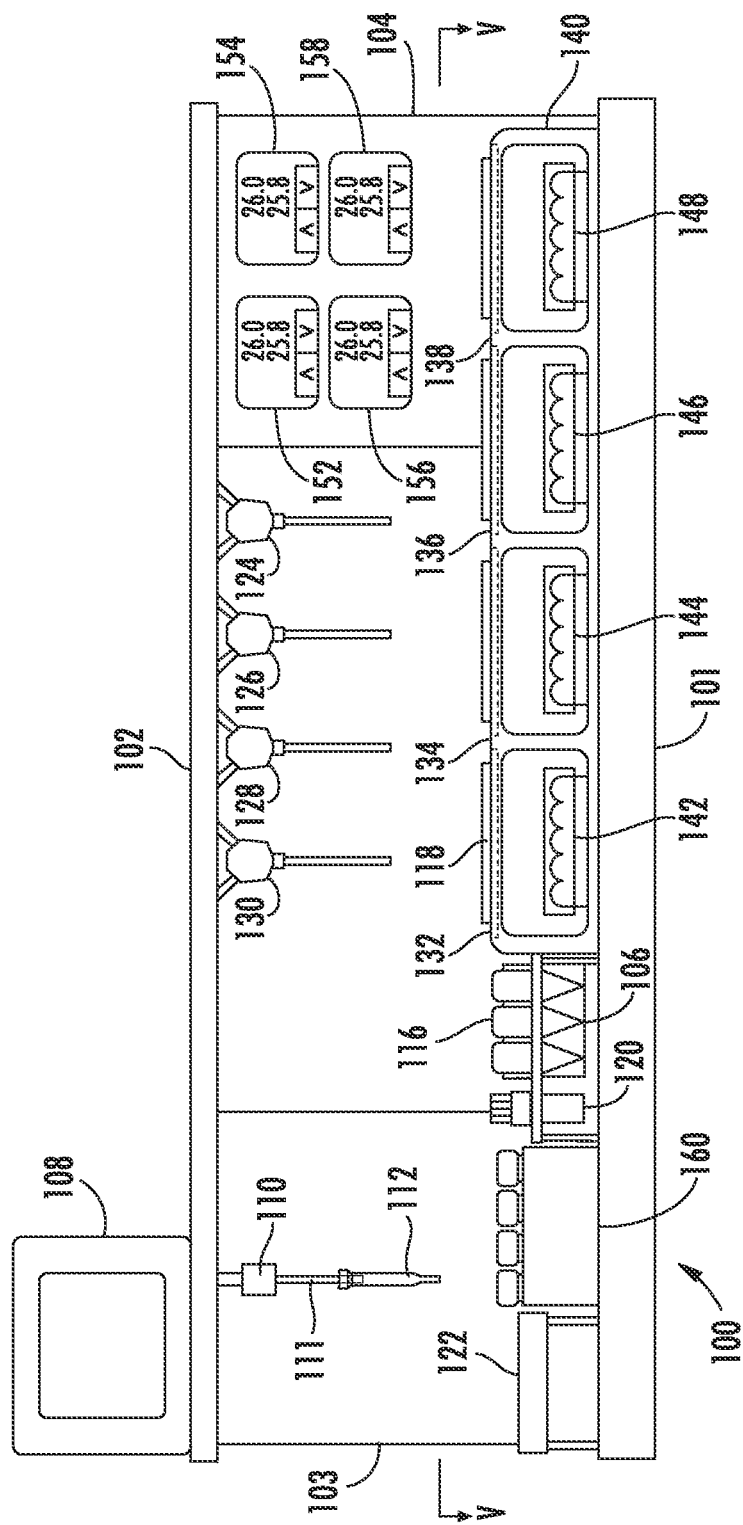
Figure 5:
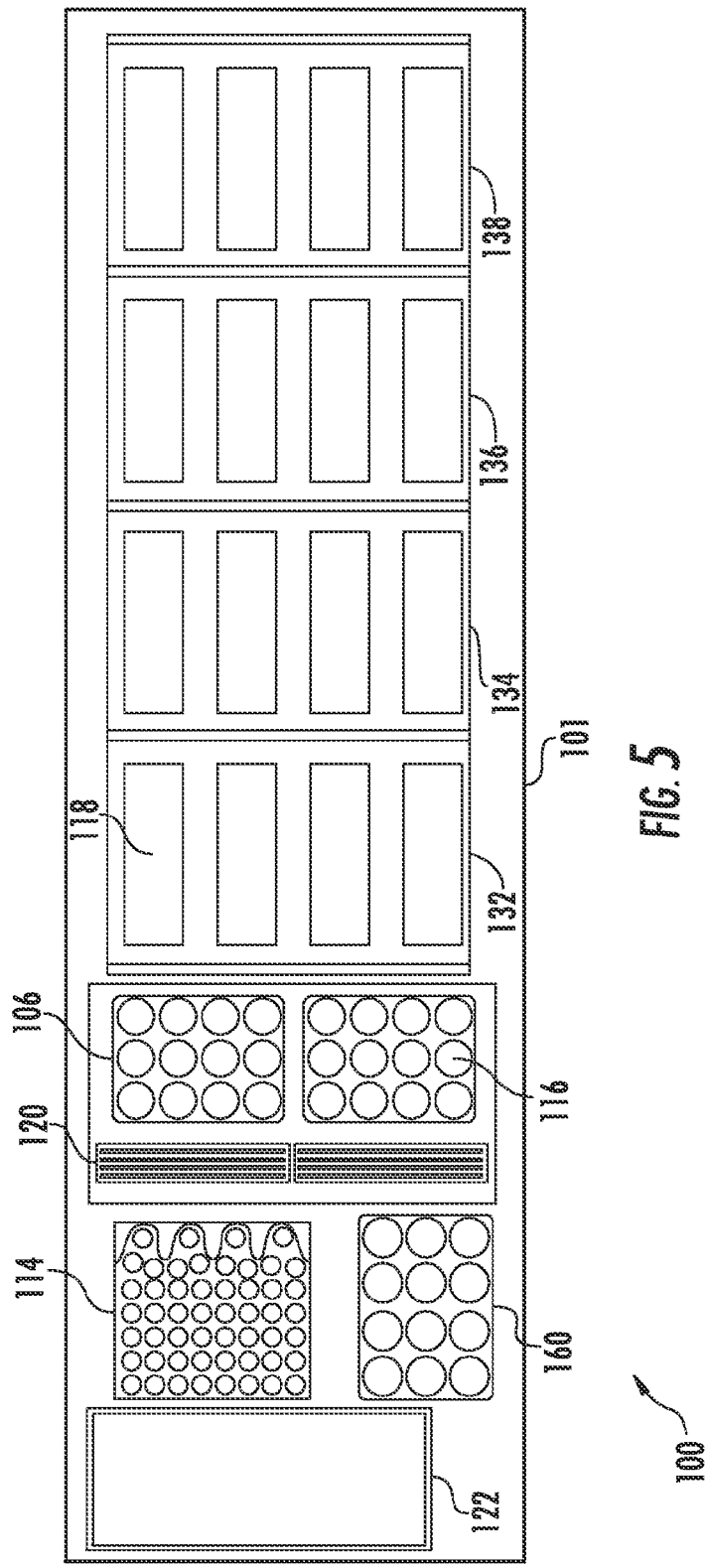
Figure 6:
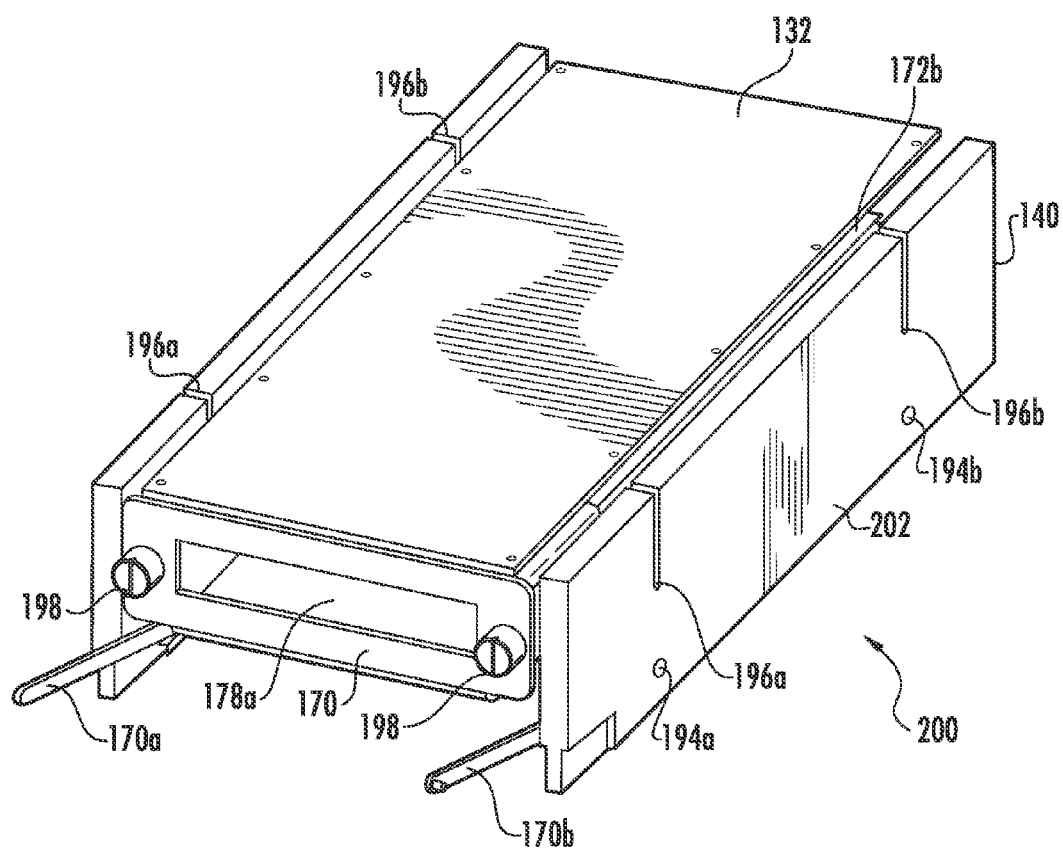
Figure 7:
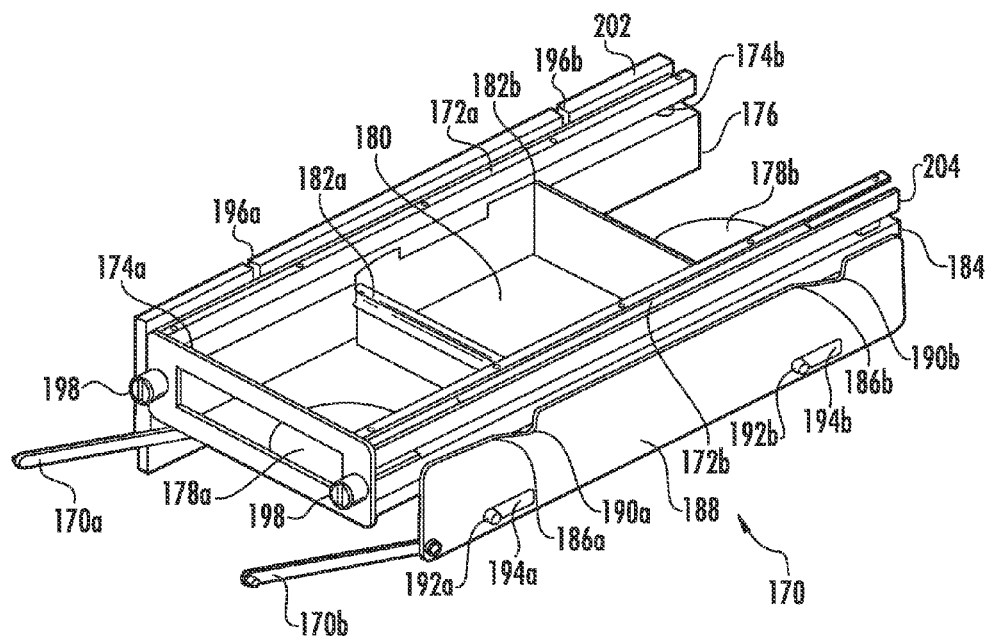
Figure 8:
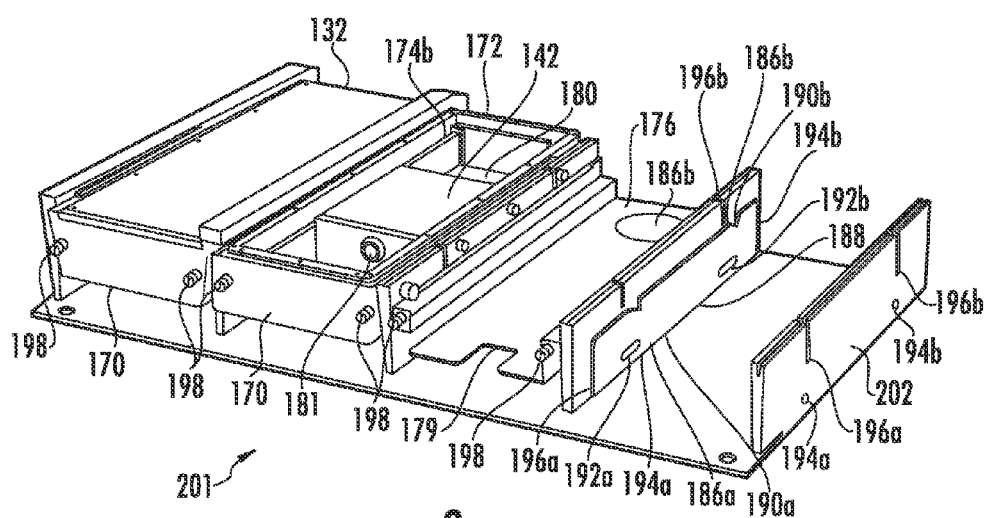
Figure 9:
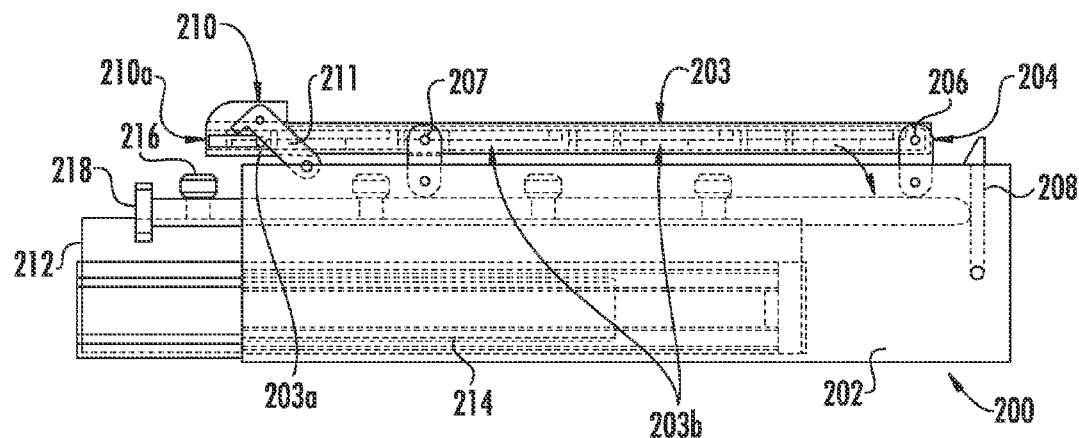
Figure 10:
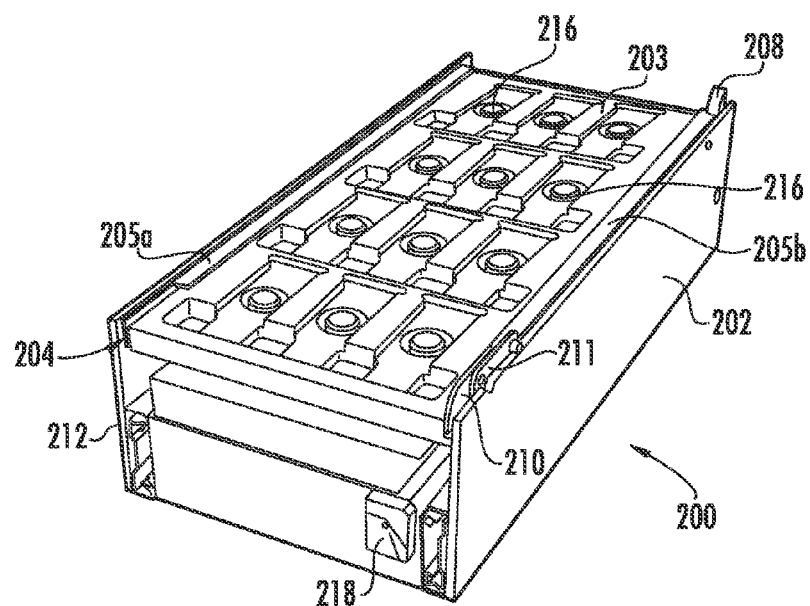
Figure 11:
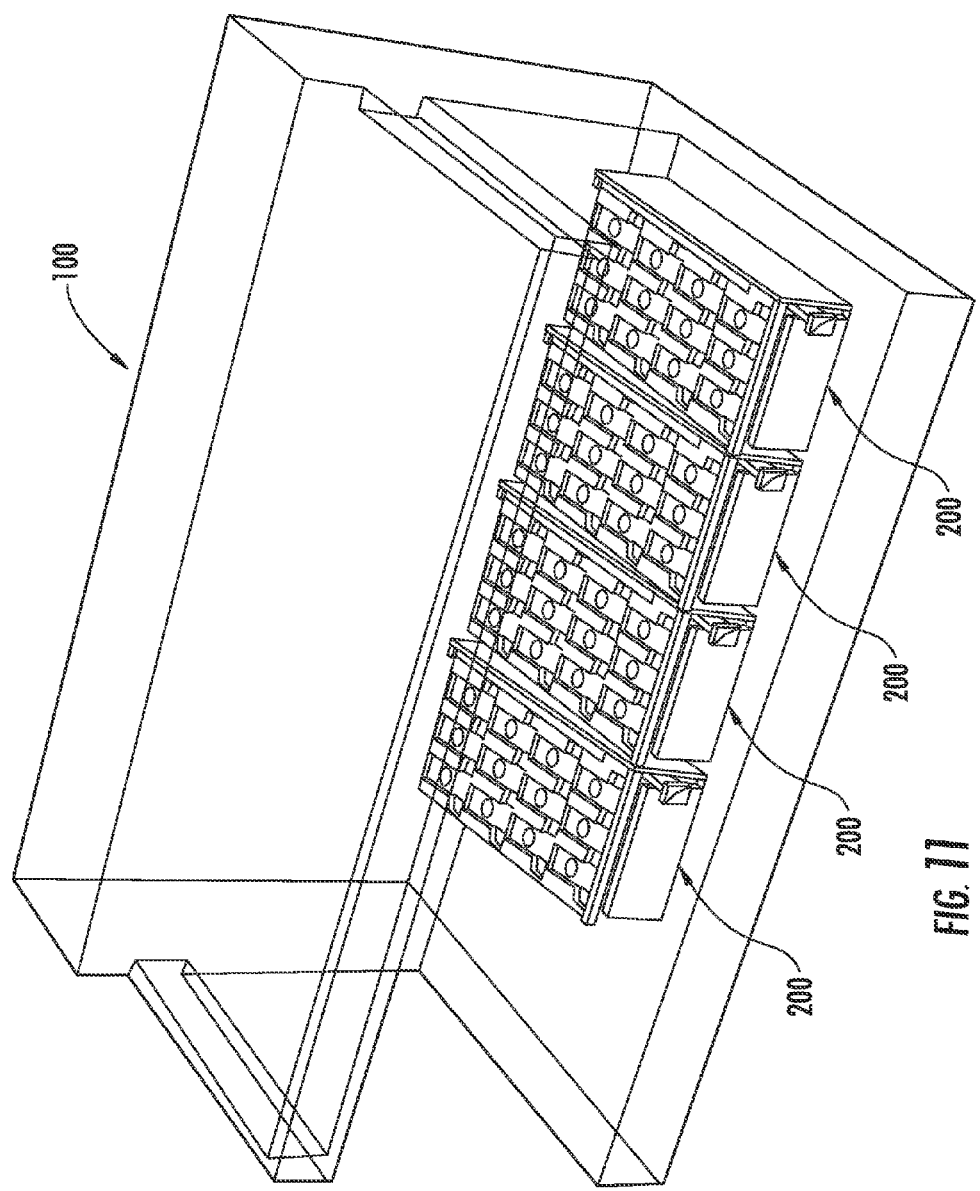
Figure 12:
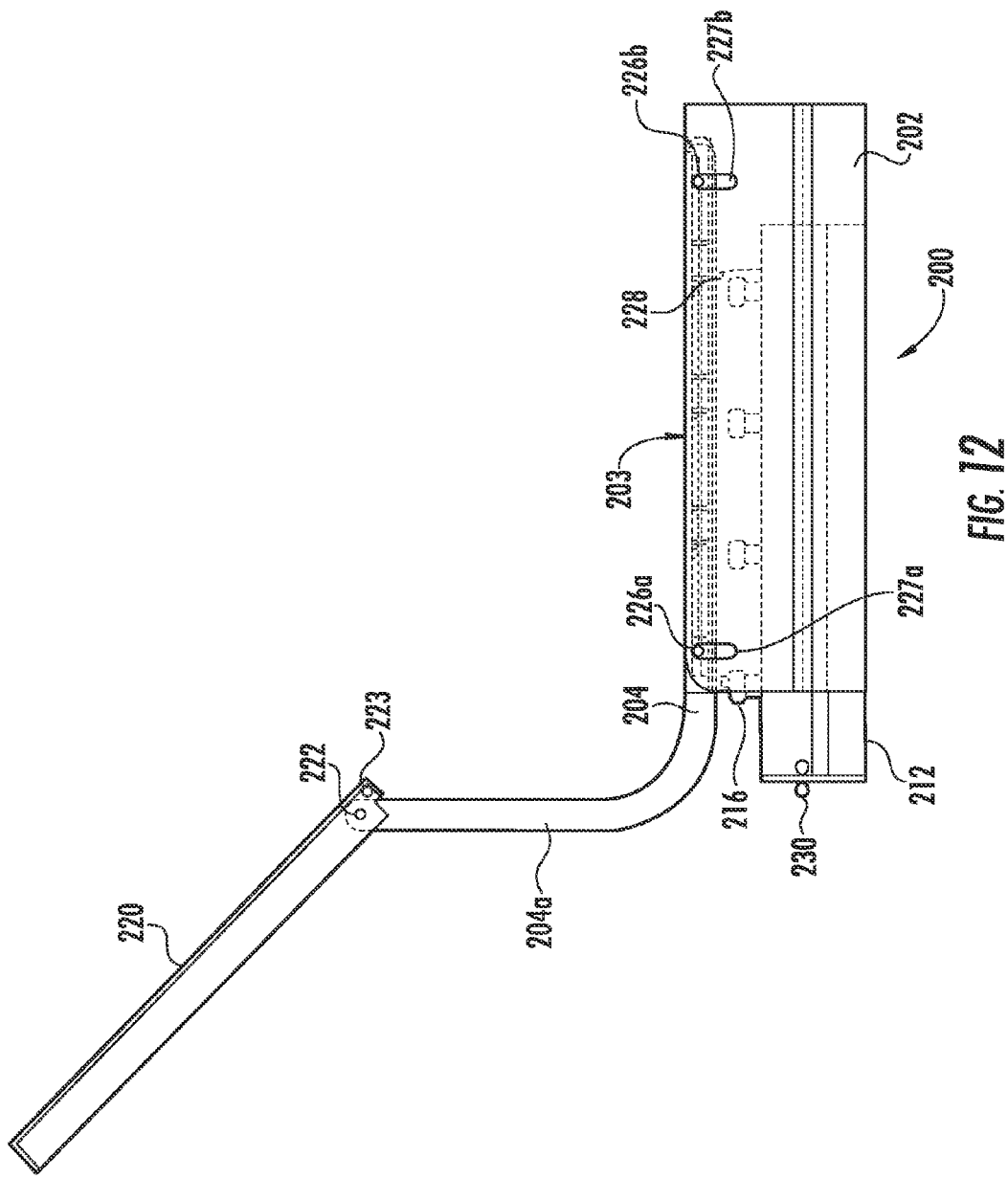
Figure 13:
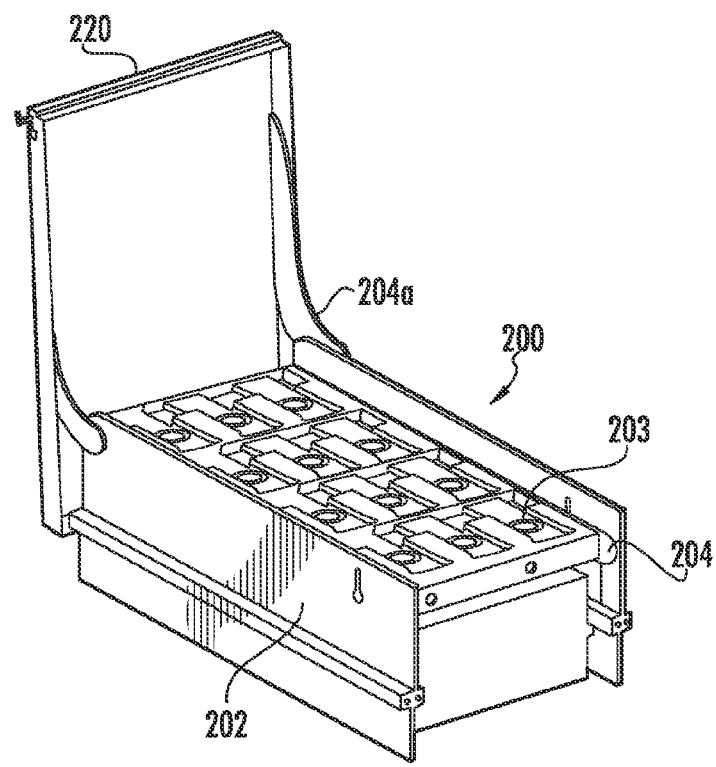
Figure 14:
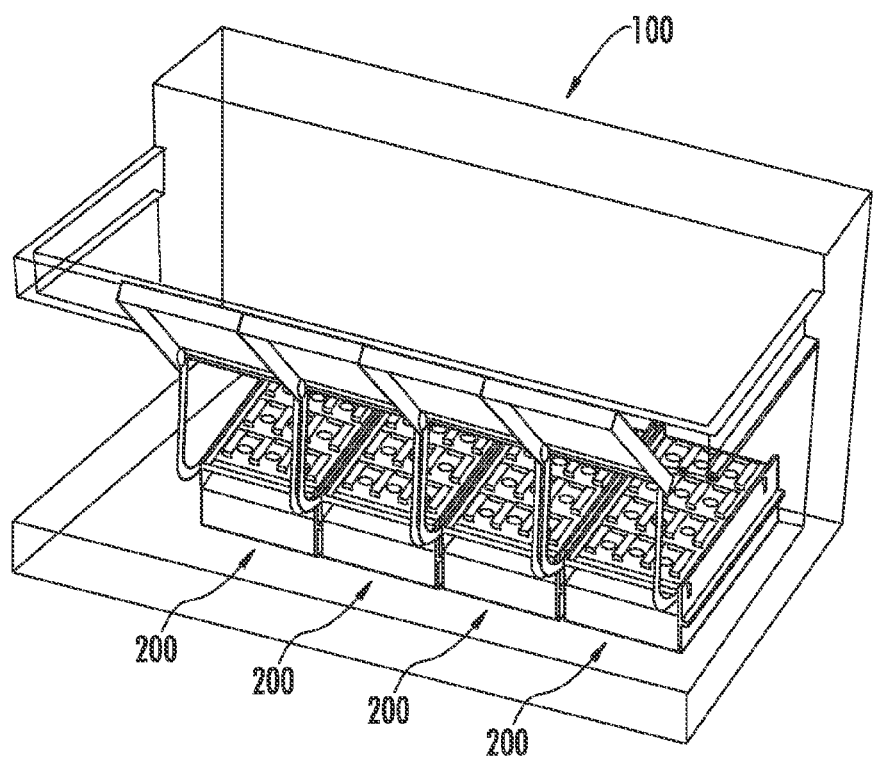
Figure 15:
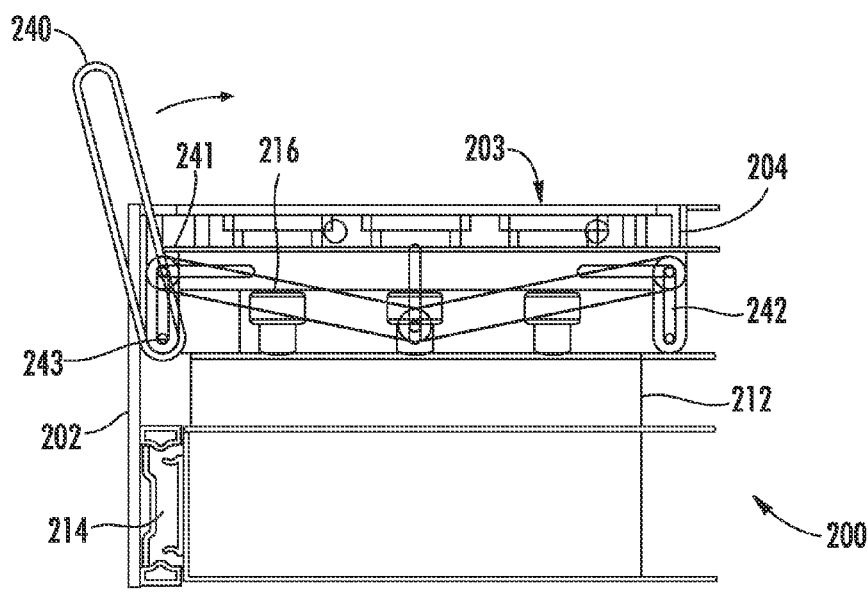
Figure 16:
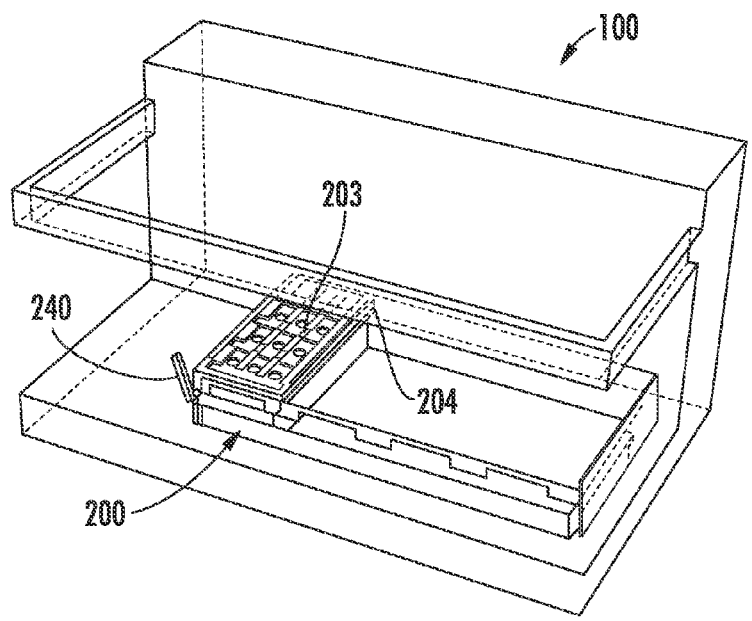
Figure 17:
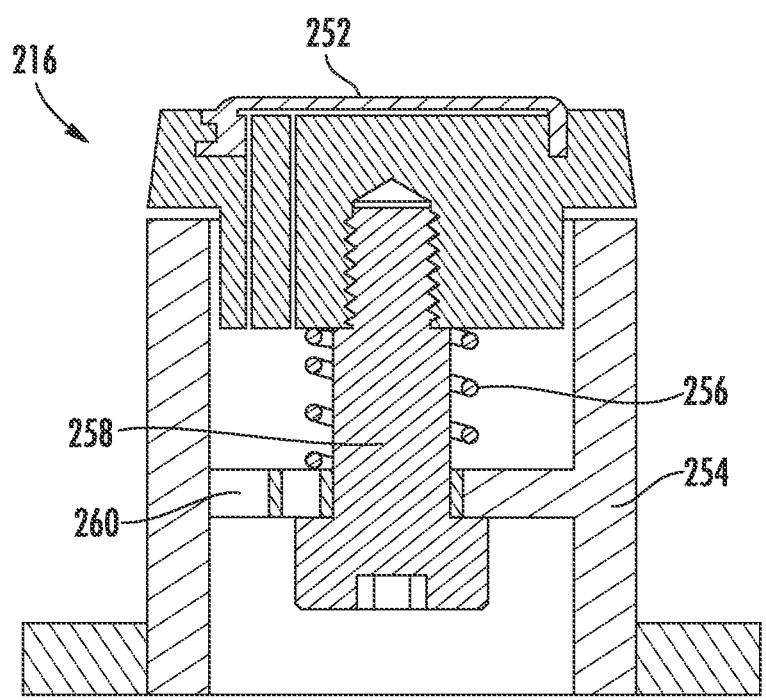
Figure 18:
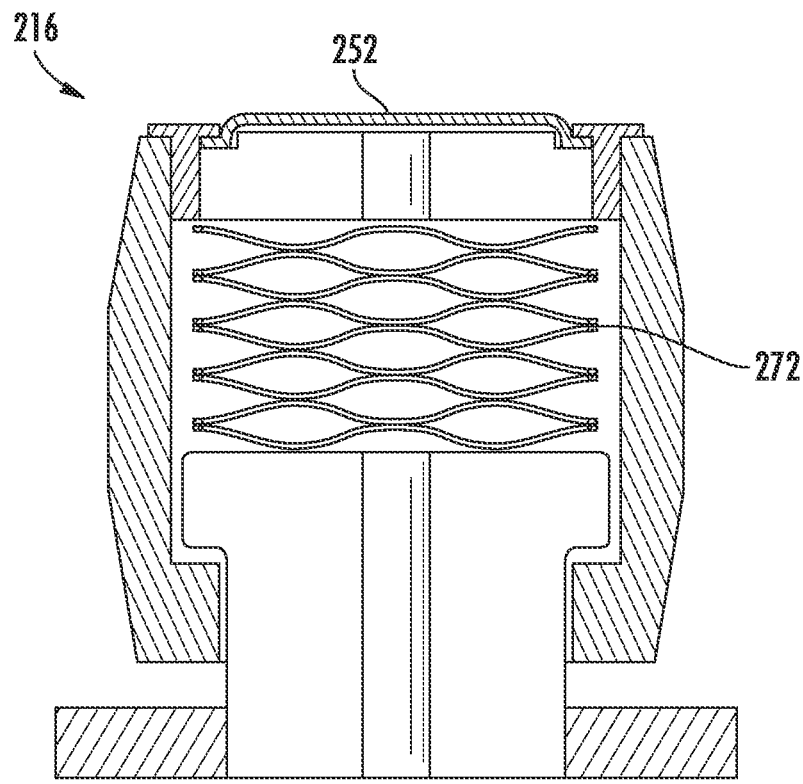
Figure 19:
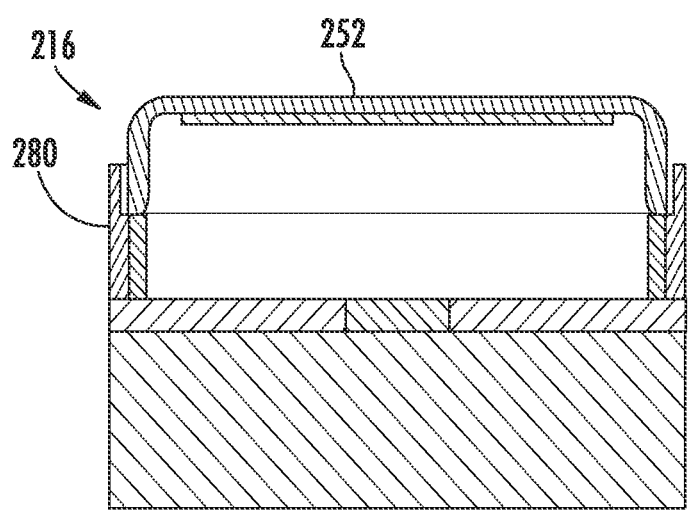
Figure 20:
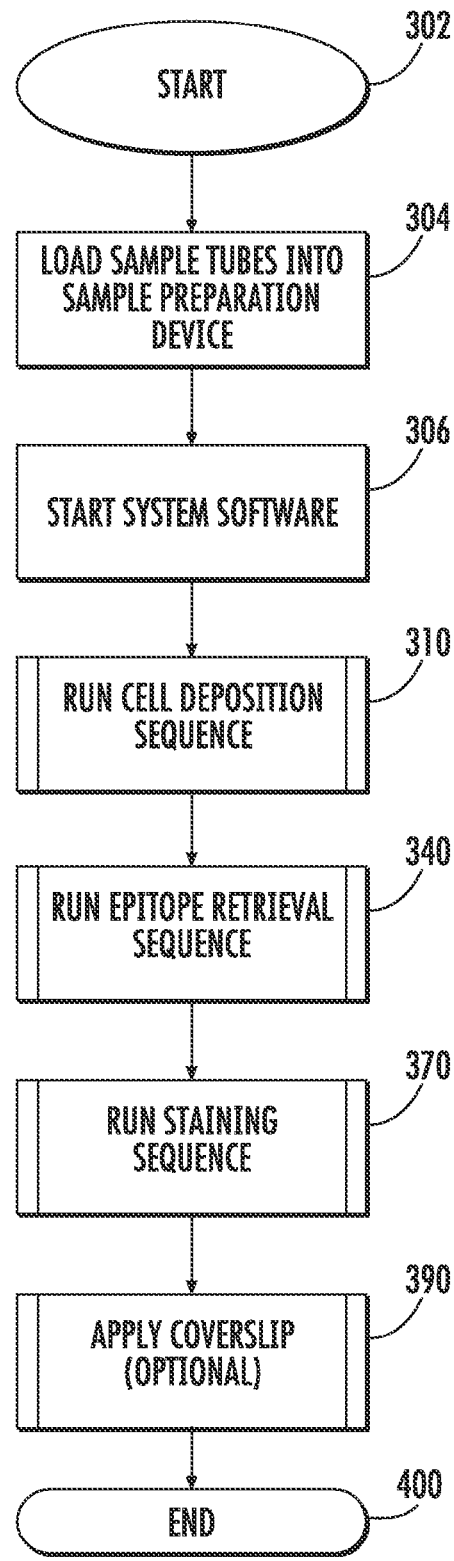
Figure 21:
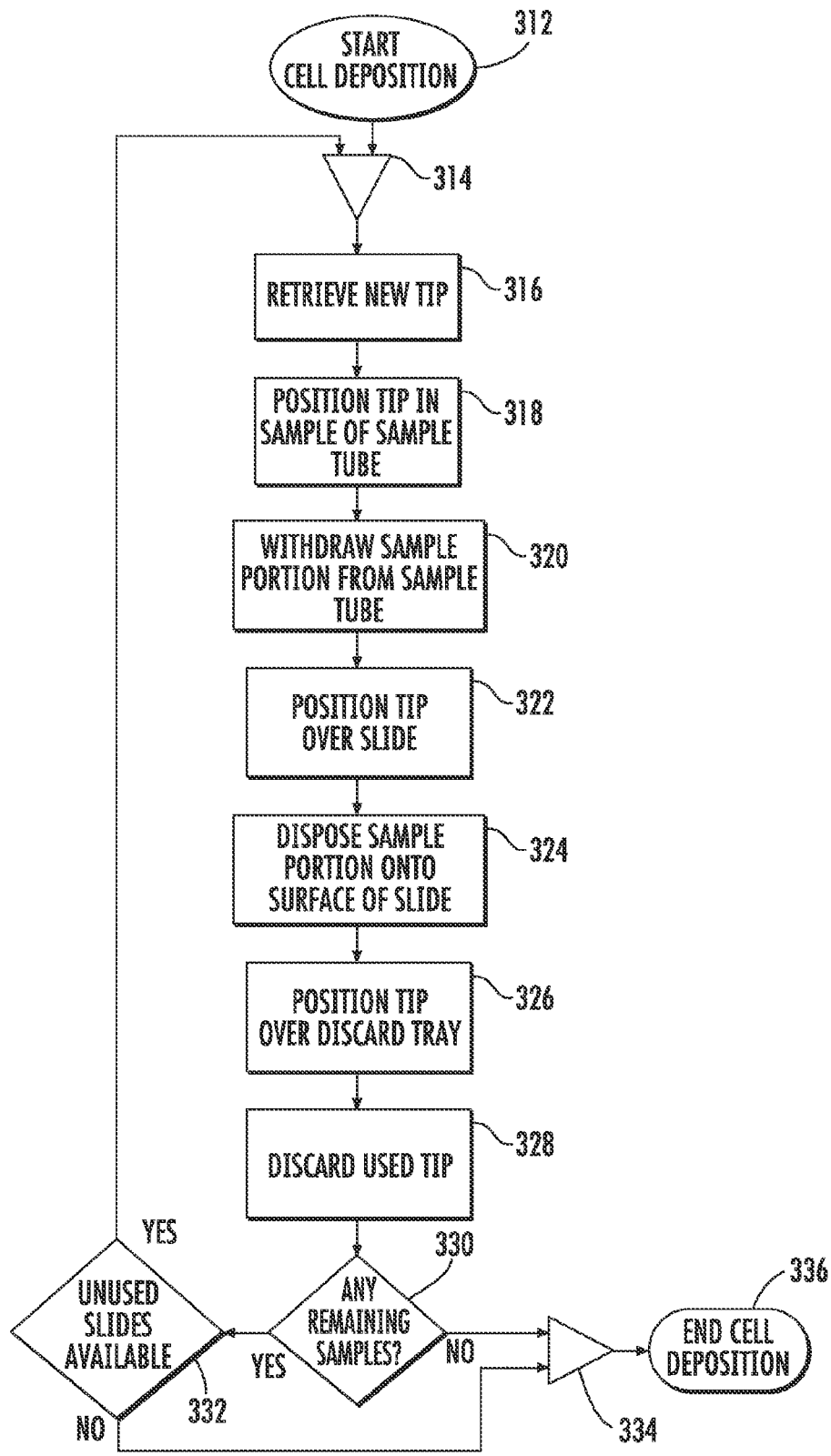
Figure 22:
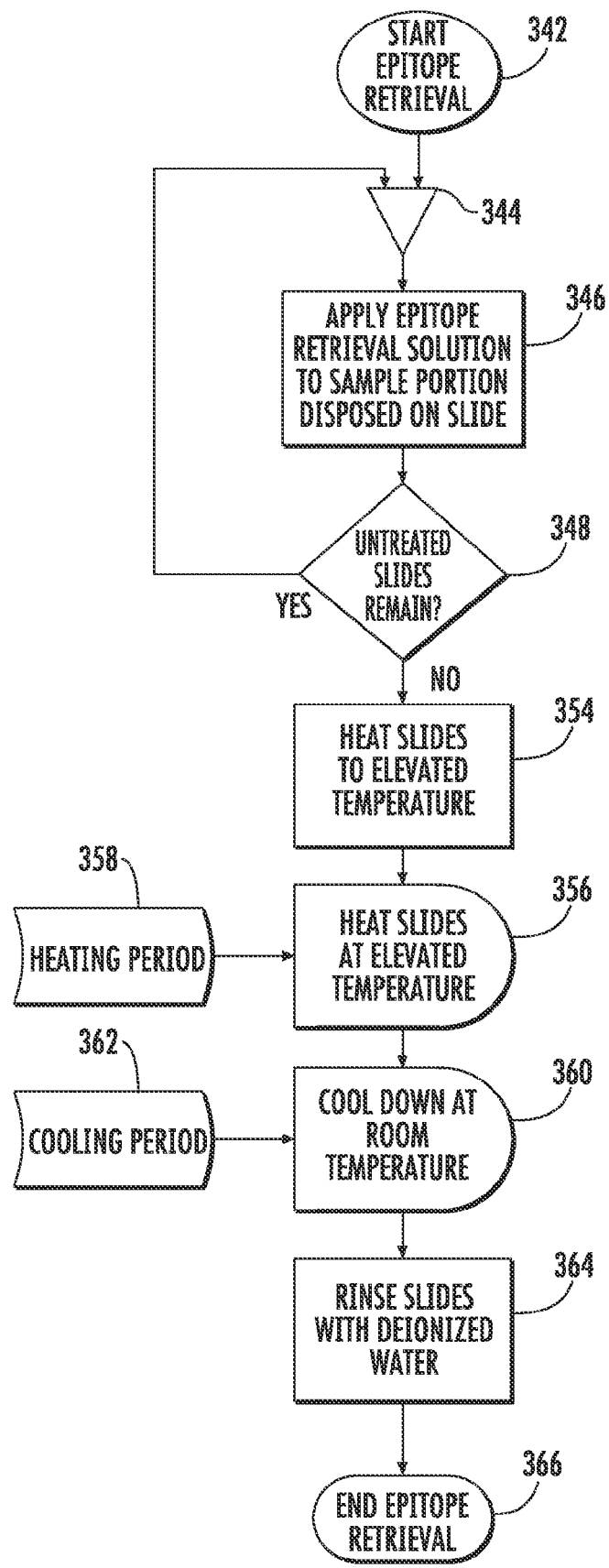
Figure 23:
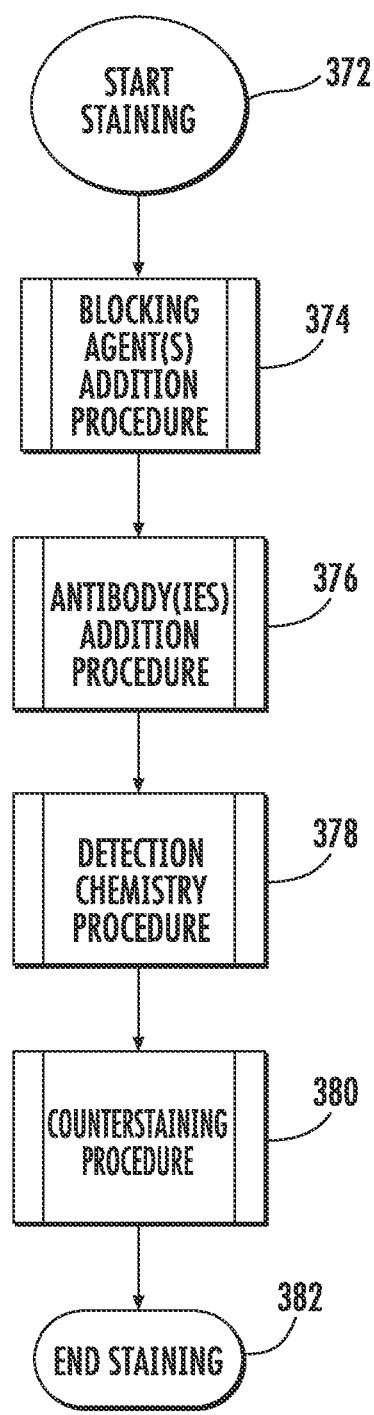
Figure 25:
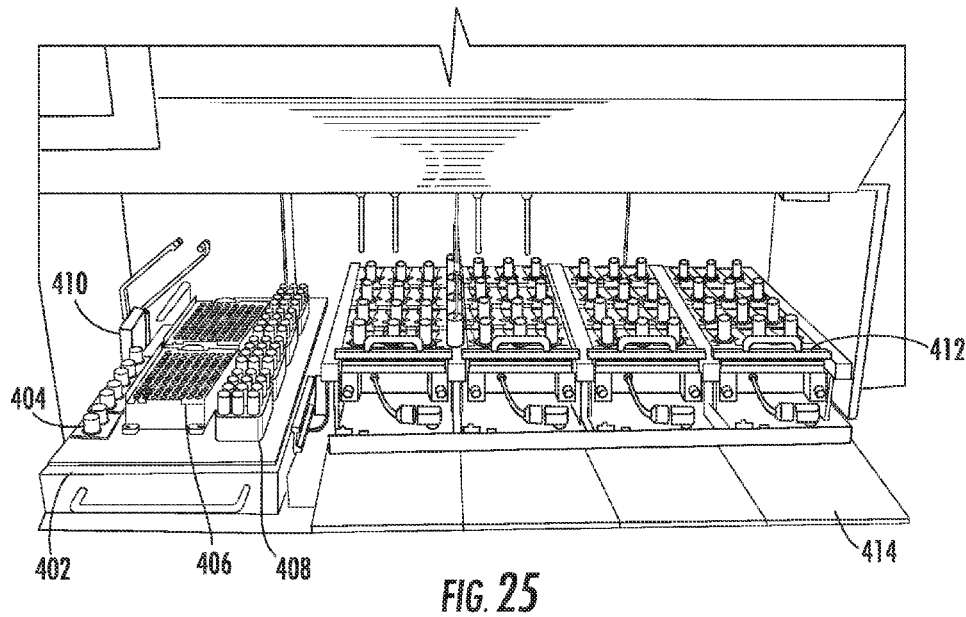
Figure 24:
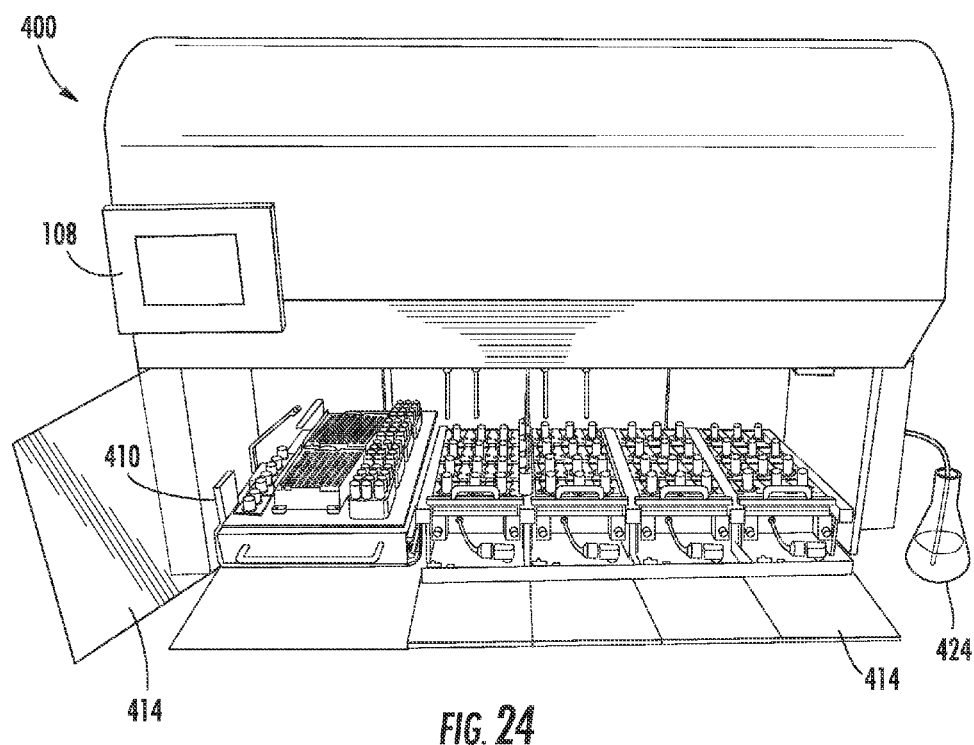
Figure 26:
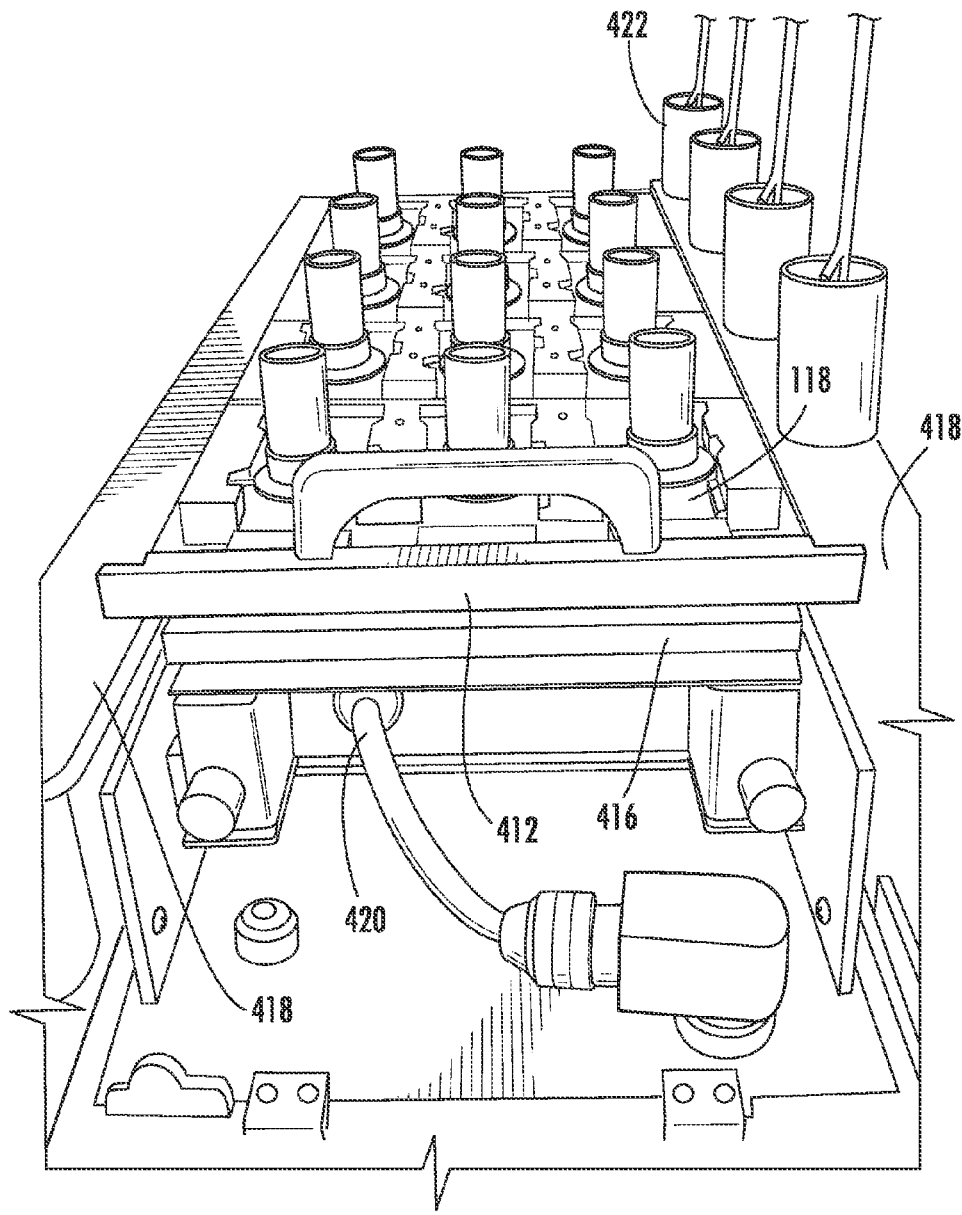
Figure 27:
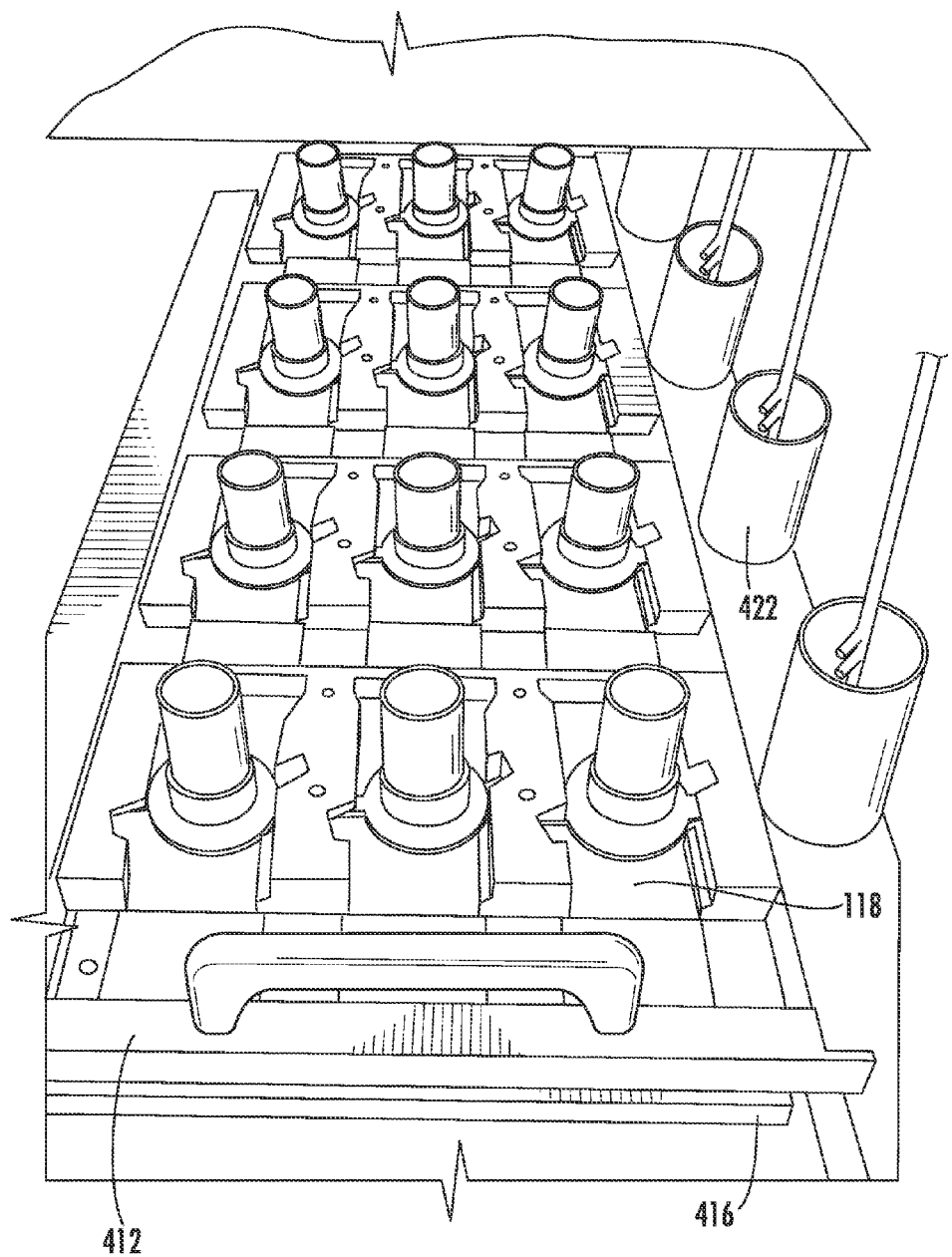
Figure 28:
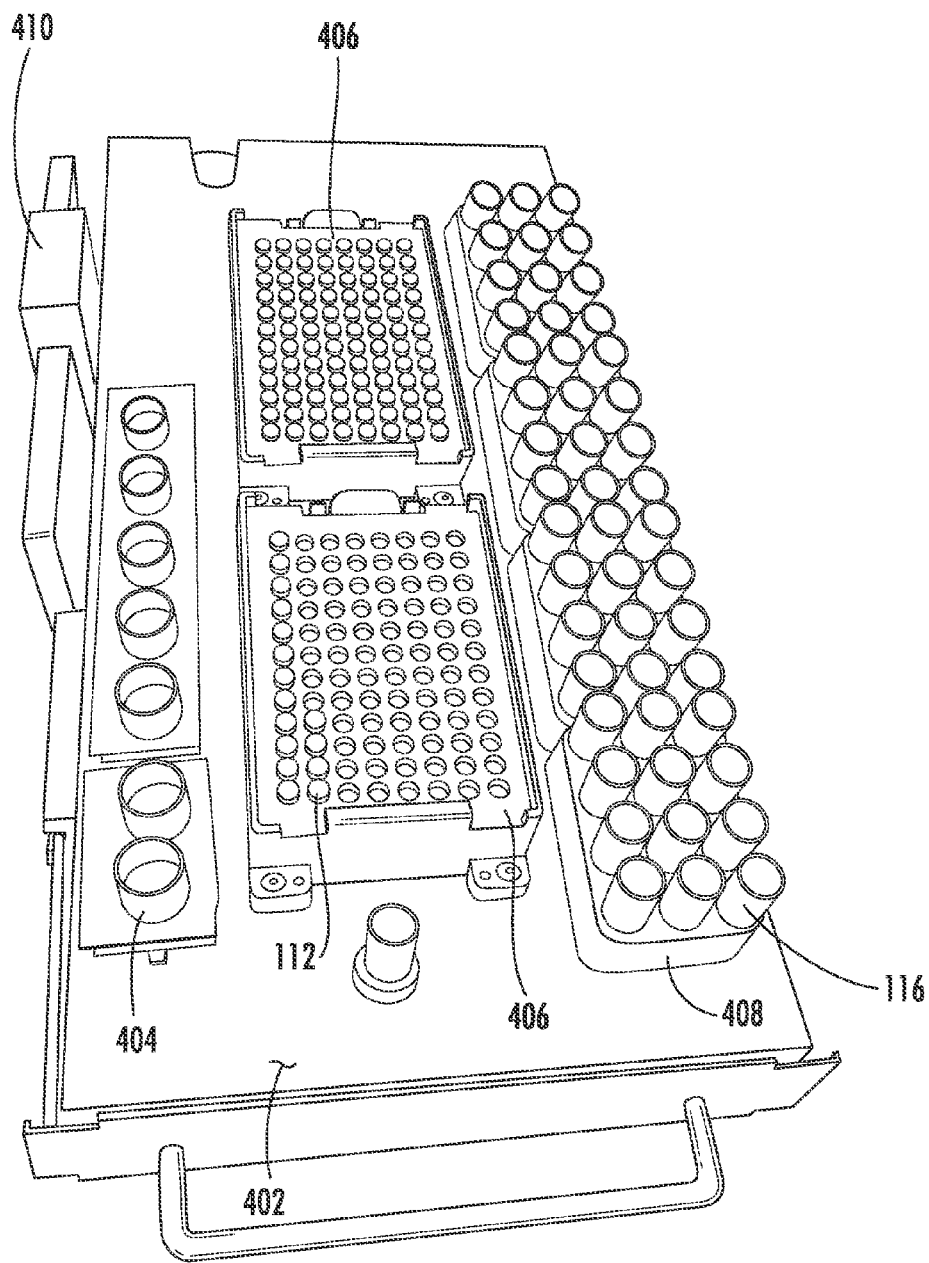
Figure 29:
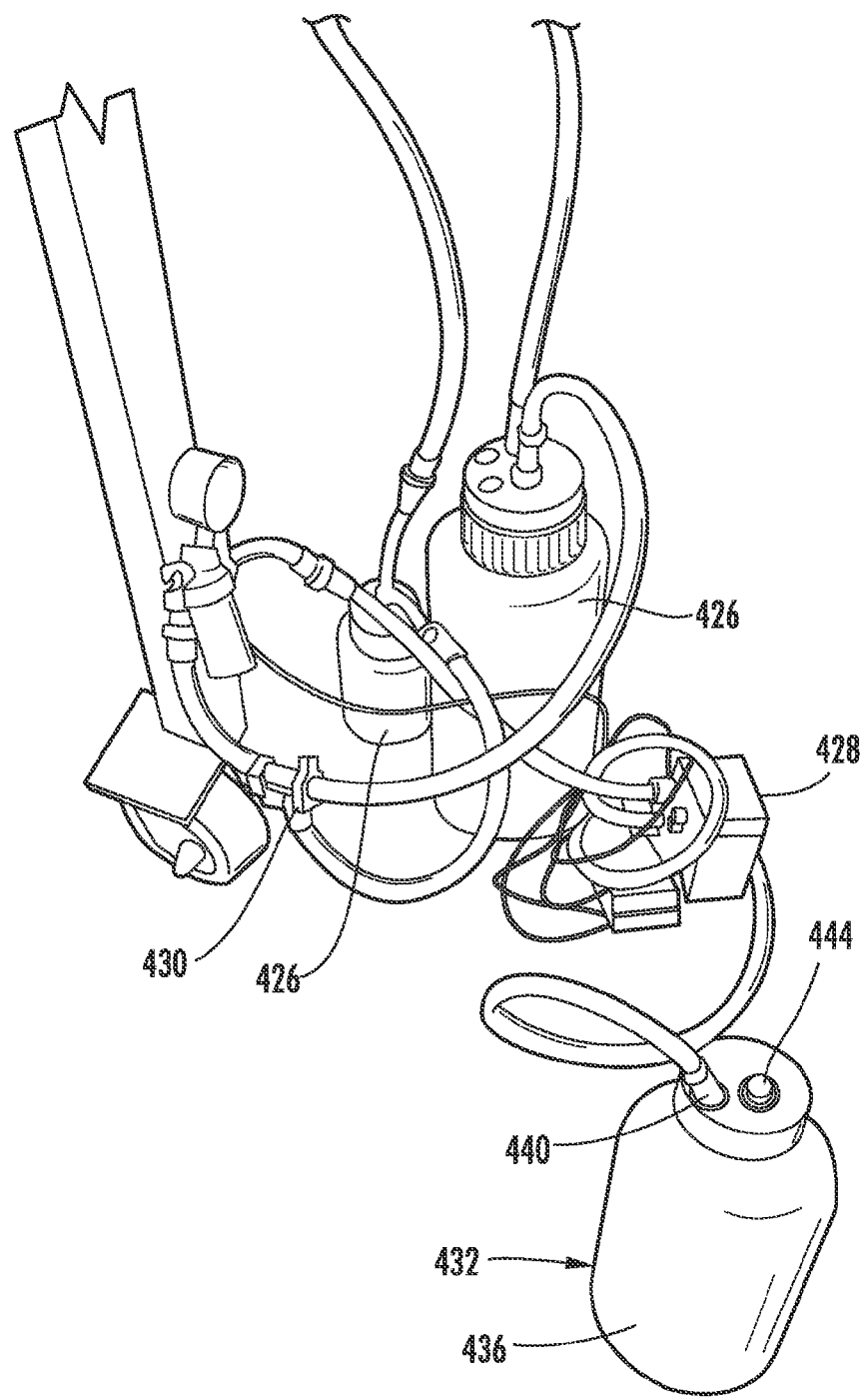
Figure 30:
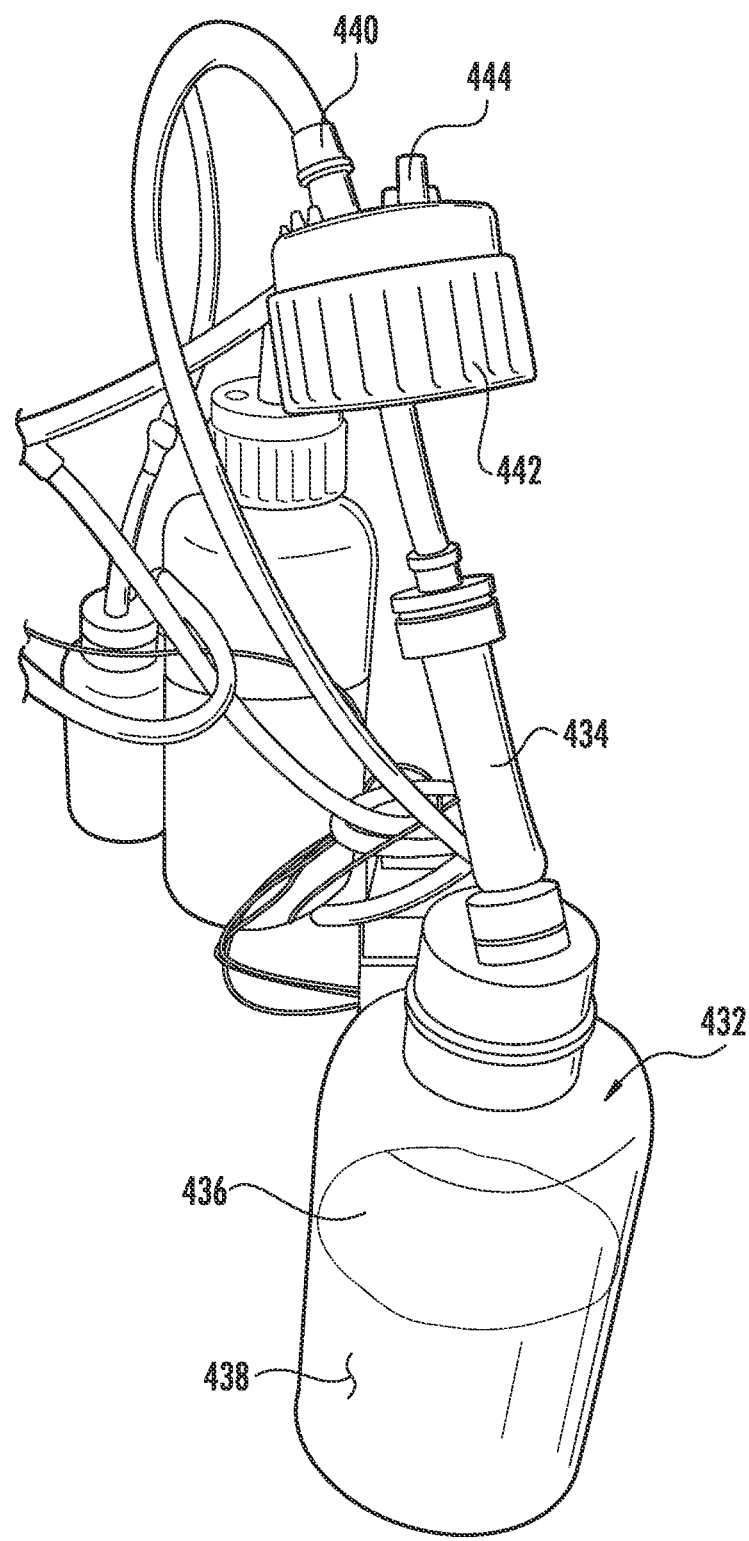

Having thus described the invention in general terms, reference will now be made to the accompanying drawings, which are not necessarily drawn to scale, and wherein:

FIG. 1 is a flowchart showing the general components of a sample preparation device, according to one aspect of the present invention;

FIG. 2 is a flowchart showing details of some components of a sample preparation device, according to one aspect of the present invention;

FIG. 3 is a perspective view of a sample preparation device, according to one aspect of the present invention;

FIG. 4 is a side view illustrating an embodiment of a sample preparation device, according to one aspect of the present invention;

FIG. 5 is a section view taken along the V-V line of FIG. 4 illustrating a sample preparation device, according to one aspect of the present invention;

FIG. 6 is a perspective view of a heating module assembly for a sample preparation device, according to one aspect of the present invention;

FIG. 7 is a perspective view of a carriage assembly of a heating module assembly for a sample preparation device, according to one aspect of the present invention;

FIG. 8 is a perspective view showing a heating module assembly in multiple gradated forms of assembly for a sample preparation device, according to an aspect of the present invention;

FIG. 9 is a side view of a heating module assembly for a sample preparation device, according to another aspect of the present invention;

FIG. 10 is a perspective view of a heating module assembly for a sample preparation device, according to another aspect of the present invention;

FIG. 11 is a perspective view of a plurality of heating module assemblies mounted in a sample preparation device, according to another aspect of the present invention;

FIG. 12 is a side view of a heating module assembly with an door member, for a sample preparation device according to one aspect of the present invention;

FIG. 13 is a perspective view of a heating module assembly with an door member, for a sample preparation device according to one aspect of the present invention;

FIG. 14 is a perspective view of a plurality of heating module assemblies with door member, mounted in a sample preparation device according to one aspect of the present invention;

FIG. 15 is a side view of a heating module assembly with an actuator handle, for a sample preparation device according to one aspect of the present invention;

FIG. 16 is a perspective view of a heating module assembly with an actuator handle mounted in sample preparation device, according to one aspect of the present invention;

FIG. 17 is a side view of a heating device of a heating module assembly, having a compression spring assembly, the heating device being incorporated in a sample preparation device according to one aspect of the present invention;

FIG. 18 is a side view of a heating device of a heating module assembly, having a wave spring assembly, the heating device being incorporated in a sample preparation device according to one aspect of the present invention;

FIG. 19 is a side view of a heating device of a heating module assembly, having a foam support assembly, the heating device being incorporated in a sample preparation device according to one aspect of the present invention;

FIG. 20 is a flowchart showing particular steps for preparing an immunocytochemistry assay, according to one aspect of the present invention;

FIG. 21 is a flowchart showing particular steps for cell deposition, according to one aspect of the present invention;

FIG. 22 is a flowchart showing particular steps for epitope retrieval, according to one aspect of the present invention;

FIG. 23 is a flowchart showing particular steps for staining, according to one aspect of the present invention;

FIG. 24 is a perspective view of a sample preparation device according to one embodiment of the present invention;

FIG. 25 is enlarged view of the sample preparation device shown in FIG. 24;

FIG. 26 is an enlarged view of the sample preparation device shown in FIG. 24 illustrating a support plate and heater;

FIG. 27 is an enlarged view of the sample preparation device shown in FIG. 24 illustrating a support plate supporting a plurality of slides thereon;

FIG. 28 is an enlarged view of the sample preparation device shown in FIG. 24 illustrating reagent kits, pipette tips, and sample tubes;

FIG. 29 is a perspective view of waste containers and a scrubbing muffler according to one embodiment of the present invention; and FIG. 30 is a disassembled perspective view of the scrubbing muffler shown in FIG. 29.

DETAILED DESCRIPTION OF THE INVENTION

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

Aspects of the present invention, as disclosed herein, relate to a sample preparation device, more particularly, a unitary automated sample preparation device. Such a sample preparation device is generally comprised of a cell deposition module, an epitope retrieval module, and a staining module. The epitope retrieval module may be employed, for example, in the preparation of immunochemistry, more particularly, immunocytochemistry, assays. Other modules may be incorporated, as needed, into aspects of the device to be used only when necessary for preparing a particular sample. As used herein, the term "module" may refer to an individual component of a system, either fixed or interchangeable, or an instrument or device, or collection thereof, for performing one or more identifiable functions. The term "module" may encompass any component, instrument, or device, or collection thereof, which is capable of performing one or more individualized functions or one or more overlapping functions in relationship to other modules that may be included in or integral to a given system. A "module" may have one or more components, instruments, and devices that may be unique to the module or shared with another module in the system.

The term "unitary," as used herein, refers to a substantially integrated unit that may formed of separate parts, which cooperate to perform a coordinated function. For example, reference to a "unitary sample preparation device" refers to the collection of modules, components, instruments, and/or devices that cooperatively function in order to prepare a sample according to an assay protocol.

In some instances, aspects of the sample preparation device, may include an analyzer device for analyzing the prepared sample. In yet other embodiments, the components of the disclosed aspects of the sample preparation device may be incorporated into, or otherwise integrated to form, a unitary apparatus having a single minimized footprint, the unitary apparatus capable of providing, among other things, cell deposition and antigen retrieval for detection and ensuing diagnosis.

In some embodiments, aspects of the sample preparation device can be useful for preparing and/or processing a sample taken from a human or animal subject, such as a cytological sample. Indeed, aspects of the sample preparation device may be used to prepare and/or process an assay device supporting a specimen that is to undergo further post-preparation analysis. Some particular aspects of the invention may be directed to preparing and/or processing a sample according to any immunochemistry, for example, an immunocytochemistry, protocol. One aspect of the sample preparation device is directed to the capability of simultaneously processing a plurality of samples (e.g., cytological samples or histological samples), each supported by a separate assay device, using an assay procedure selected from any number of assay procedures capable of being performed.

According to some aspects, embodiments of the invention may provide improvements over conventional sample preparation systems known in the art, for example, by increasing operational efficiencies with increased throughput, improving the precision of the analytical process, and decreasing the footprint of the device used to prepare a sample. Further improvements addressed by certain aspects of the present invention may also include lowered operator training requirements, reduced or minimized sample amounts needed to produce the desired assay, and decreased or minimized human/operator contact with the sample during preparation thereof.

A flowchart showing the general components one embodiment of the sample preparation device according to the invention is shown in FIG. 1. In this exemplary embodiment, a sample 5 is introduced to the sample preparation device 100, from which an assay device 50 is prepared and the sample assayed according to a selected assay protocol. The prepared assay device 50 may allow or otherwise facilitate further analysis of the sample 5 such as, for example, through visual inspection/examination, with or without a microscopy device, or through other suitable examination and/or analytical procedures. Aspects of the sample preparation device 100 may comprise a cell deposition module 10. The term "cell deposition" as used herein is directed to depositing or disposing a sample, a specimen, or a portion thereof, onto an assay device. In one embodiment of the invention the assay device is a slide, such as a microscope slide. In one embodiment of the invention, the sample, the specimen, or portion thereof, is deposited on the slide as a cell monolayer. In some instances, the cell monolayer may be a substantially continuous distribution of cells across a surface of the slide. In one embodiment of the invention, the sample is a cytological sample. In other embodiments of the invention, the sample is a histological sample. In embodiments of the invention, the assay protocol is any immunochemistry protocol. In certain embodiments of the invention, the assay protocol is an immunocytochemistry assay protocol. In still other embodiments of the invention, the assay protocol is an immunohistochemistry protocol. In some embodiments of the invention, the cell deposition module 10 is configured to deposit the desired portion of the sample onto the slide. Optionally, the slide may include a well for holding the sample portion that has been transferred to the slide. In some instances, the slide includes a material that allows the sample to become adhered to the slide.

In one embodiment of the invention, the sample to be processed is obtained from a collection device, such as a swab, broom-type sampling device, brush, or other suitable device, either prior to or as part of the cell deposition procedure. The manner in which the sample is obtained from the collection device can be a manual procedure, but an automated procedure may be more desirable in order to, for example, avoid sample contamination. In other embodiments of the invention, the sample to be deposited or disposed on an assay device may be in the form of a fluid contained in a sample vial or other sample container, collectively referred to herein interchangeably as a "sample vial" or "sample tube." In some instances, the sample collection process is a direct-to-vial collection method to minimize human contact with the sample and to prevent sample contamination. Optionally, in some embodiments of the invention, an indicia of reference or other device for identifying the sample may be applied to the sample vial holding the sample. Also, an indicia of reference or other device for identifying the sample may be applied to the assay device or slide receiving the sample portion for further analysis.

A sample identification module may be used to confirm the sample has been properly identified and, optionally, to ensure the sample portion is from the desired sample at the time an assay device is prepared with the sample or a portion thereof. In one exemplary embodiment of the invention, the sample identification module may be configured to visually scan the sample vial, container, other sample holding device, or assay device for the indicia of reference. In another exemplary embodiment of the invention, the sample identification module may be configured to implement an electronic device for reading the indicia of reference or other device for identifying the sample, in order to identify the sample contained therein or disposed thereon. In other exemplary embodiments of the invention, the sample identification module may be configured to implement more than one scanner, reader, or the like, and any combination thereof for identifying the sample. In other embodiments of the invention, the sample preparation device 100 may additionally comprise a plurality of sample identification modules to provide, for example, continuous sample tracking. Accordingly, various embodiments of the invention may provide automated tracking of the sample, as the sample is prepared by and in the sample preparation device, along with the capability of mapping the progress of the sample and providing chain-of-custody validation of the sample, if needed.

Additionally, some other identification (ID) can be assigned to the sample. For example, the ID assigned to the sample can be an ID that is assigned by the forwarding hospital, clinic, or other medical provider. In one embodiment of the invention, the ID is uniquely assigned by the sample preparation device. In another embodiment of the invention, the ID that is uniquely assigned by the sample preparation device is characteristic of the laboratory that processes the sample. In another embodiment of the invention, the ID is an internal assignment provided by the laboratory preparing the sample, for example, for tracking the sample in the laboratory. Irrespective of the method for assigning the ID to the sample, the sample preparation device can be configured to cross-match the ID with the sample prepared by the sample preparation device 100.

The indicia of reference or other sample identification may be, for example, a visually-perceptible indicia, a machine readable indicia such as a bar code, a symbol or graphic that can be visually and/or automatically detected such as with color schemes or some other structure identification, a magnetic electronic surveillance device such as a magnetic strip, a radio frequency tag, and other similar devices. The ID assigned to the sample may also be used to access to other information concerning the sample such as, for example, the type of the sample; the origin of the sample; identification number(s) assigned by the originator of the sample; instructions for handling the sample; billing information; date the sample was obtained; date when results are desired; information relating to the human or animal from which the sample was obtained; other samples associated with the sample, if any; criticality of the sample; type of results desired for and/or analyses to be performed on the sample; and combinations thereof.

According to one embodiment, a barcode is associated with each sample tube 116. For example, a barcode may be attached to a sample tube 116 prior to performing pre-processing steps or otherwise loading the samples tubes into the sample preparation device 100. In addition, sample slides 118 may include corresponding barcodes. The sample tube 116 barcodes may be scanned when placed into a sample rack 106 or centrifuge tube holder during the pre-processing steps and stored in a data file. In one aspect, the sample tubes 116 are scanned in a particular order. Moreover, the centrifuge tube holder may include an RFID tag associated therewith which contains a unique identifier and a barcode reflecting this unique identifier. The RFID barcode may be used for redundancy or as a secondary verification means for the unique identifier. A data system may be used to create a data file merging the sample tube barcodes with the RFID identifier, which may also include information regarding the location of the sample tubes. Alternatively, the sample tube 116 barcodes may be written onto the RFID tag, which may be read and used to create a data file. In particular, the barcodes for the sample tubes 116 may be written to the RFID tag such that the sample tube barcodes and/or locations may be determined by reading the RFID tag such as when loading the sample tubes into the sample preparation device 100. Where the RFID tag is written with the sample tube barcodes, the sample tubes may be used with any sample preparation device 100, rather than being limited to a sample preparation device that is registered to receive a particular centrifuge tube holder.

A data file may be created for each run of the sample preparation device 100. As the centrifuge tube holder is loaded into the sample preparation device 100, an RFID reader will register the unique identifier and tube holder position. For instance, the RFID tag may be located on the bottom of the centrifuge tube holder, and a window defined below the tube holder may allow an RFID reader to read the RFID tag as the centrifuge tube holder is loaded into the sample preparation device. The RFID reader can read the unique identifier on the RFID tag and/or position of the centrifuge holder as the sample rack is positioned in the sample preparation device 100 to verify that the correct tube holder is present and in the correct location. Where the tube holders are positioned on a slidable drawer, the RFID reader can sequentially read corresponding RFID tags as the drawer is advanced into the sample preparation device.

A barcode reader may then be utilized to read barcodes on the assay devices 118, such as sample slides, to register the barcodes and/or locations of the sample slides, which can be stored in a slide layout data file. For example, a barcode reader may be mounted to the transfer assembly 110. The sample preparation device 100 is configured to compare the sample slide barcodes in the slide layout data file with the sample tube barcodes contained in the tube data file stored previously. In one embodiment, if the sample preparation device 100 determines that the sample tubes are properly sequenced with the sample slides, further processing of the sample tubes is performed. Otherwise, the process will pause, and an operator can be alerted of the error. In another embodiment, if the sample slide barcodes correspond to the barcodes in the data file, the sample preparation device 100 transfers the samples to the correct slide position, regardless of position or alignment. If the sample slide barcodes do not match the barcodes in the data file for the sample tubes, the process will pause, and an operator may be notified.

Aspects of the sample preparation device 100 can further comprise an epitope retrieval module 20. Such an epitope retrieval module 20 may be desirable in certain embodiments of the sample preparation device 100, for example, when processing and/or preparing a sample or portion thereof in accordance with an immunocytochemistry protocol or an immunohistochemistry protocol. As used herein, the term "epitope" indicates a localized region of an antigen that is capable of combining with a specific antibody to counter any immune response that may otherwise occur.

As used herein, the term "epitope retrieval" refers to a procedure used to chemically prepare the localized regions or epitopes of a cell surface antigen in order to allow them to be more easily identified. In some instances, an epitope retrieval procedure may allow these localized regions of the sample to become visibly distinguishable, whether or not a subsequent staining procedure is applied thereto. The antigen retrieval methods of some embodiments of the invention assist with the ability to better detect antigens that may be present in a sample. Antigenic sites that can otherwise go undetected, for example, may be revealed by breaking some of the protein cross-links surrounding the antigen. Enzymes may be applied to the sample in order to allow for these antigens to become revealed. A process known as heat induced epitope retrieval, whereby the sample is heated for a certain amount of time, may also be used.

Aspects of the sample preparation device 100 may further comprise a staining module 30. In one embodiment of the invention, the staining module 30 may be configured to implement at least one reagent that, when applied to the sample, may facilitate or promote visualization of the cells of the sample that have been deposited or disposed on the assay device. In some embodiments of the invention, the sample preparation device 100 may comprise a staining module 30 configured to implement at least one reagent addition sequence or a combination of sequentially applied reagent treatments to promote visualization of the cells of the sample that are deposited or disposed on the assay device.

As shown in FIG. 1, optionally, the sample preparation device 100 may comprise a module configured to place a coverglass or coverslip 40, both terms being used interchangeably herein, onto the assay device in order to cover at least a portion (i.e., the portion having the sample deposited thereon) of the prepared assay device 50. In some instances, for example, with respect to embodiments of the invention in which the assay device is a slide, certain additional procedures may be used to promote adhesion of the deposited sample portion to the slide.

FIG. 2 is a flowchart showing more details of components of a sample preparation device according to one embodiment of the invention for depositing or disposing a sample (or sample portion) 5 onto an assay device 50. According to such an embodiment of the invention, as shown in FIG. 2, the epitope retrieval module 20 may be configured to execute a procedure for adding a buffer (or buffer solution) 21 to contact the sample disposed on the assay device. Once the sample 5 is contacted by the buffer 21, both may optionally be heated 23 to a particular temperature, via heating of the assay device 50, for a certain amount of time (step not shown). The heating procedure may comprise, for example, an initial heating (or "pre-heating") period, followed by one or more heating levels, with each level desirably being held for a particular period of time. The heating 23 of the assay device 50 may also be accomplished in conjunction with preparing/heating other similarly prepared assay devices. For example, a plurality of assay devices may be held by a single holding assembly or support assembly, wherein the entire support assembly may be heated by one or more heating devices. The assay device(s) 50 supported by and in contact with the support assembly, in turn, may be heated to a temperature approximating that of the support assembly. One skilled in the art will note that, in the preparation of a plurality of immunocytochemistry assays, it may be advantageous to heat each of the assay devices 50 (and samples disposed thereon) to substantially the same temperature when conducting particular procedures requiring heat input, such that the samples are prepared in substantially the same manner. Accordingly, the one or more heating devices may be arranged with respect to the support assembly so as to heat the assay device-interacting portions of the support assembly to substantially the same temperature such that each assay device experiences substantially the same heat input for interaction with the sample.

According to an alternate aspect of the present invention, the heating of the assay device(s) may be accomplished in different manners. For example, the support assembly may be configured to receive one or more individual heating devices in correspondence with the number of assay devices capable of being received by the support assembly. That is, the support assembly may be configured such that each assay device is heated by its own heating device. In some instances, each heating device may be configured to directly heat the corresponding assay device. Further, in some instances, the support assembly may also be configured such that the heat provided by one heating device does not affect adjacent heating devices/assay devices (i.e., each assay device is heated separately and discretely from the other assay devices). However, in such instances, the immunocytochemistry protocol may require that all assay devices be heated to substantially the same temperature. Accordingly, in such instances, the heating devices may be configured to heat each of the respective assay devices to substantially the same temperature as specified by the particular assay being conducted.

Any suitable heating device or system may be used to heat 23 the support assembly and/or the assay devices. In one example, the assay device, with the sample and buffer disposed thereon, may be supported by an aluminum support plate and a resistive heating device engaged therewith is used to increase and maintain the temperature of the support plate. In some instances, the heating device may include a controller in communication therewith that allows a pre-defined temperature of the engagement between the assay device and the support plate to be substantially consistently maintained as heat is applied to the assay device and assembly. A thermocouple or other temperature-determining device may engage the aluminum support plate to provide feedback of the actual temperature of the assembly to the controller. In other embodiments of the invention, the temperature of the assembly can be varied according to predetermined and defined temperature profile for the heating period(s). Though not shown in the exemplary embodiment of FIG. 2, a heating procedure may also be optionally performed subsequent to process steps involving the epitope retrieval module 20 and prior to process steps involving the staining module 30.

In some instances, the assay device may be subjected to a cooling step 25 prior to further processing of the sample supported by the assay device. In certain embodiments of the invention, cooling of the support assembly holding the assay device may be allowed to occur by exposure to the atmosphere at room temperature over a certain period of time after the heating device from the heating step 23 is shut down or otherwise de-actuated. In another embodiment of the invention, the support assembly and assay device are cooled through exposure to the atmosphere at room temperature until the assembly and assay device reach a certain pre-selected temperature. In yet another embodiment of the invention, the cooling step 25 may comprise actuation of a device to facilitate convective heat exchange between atmosphere and one of the support assembly, the assay device, and sample, wherein such a device may comprise, for example, a fan. In yet other embodiments of the invention, a cooling device, such as a cooling jacket, heat exchanger, thermoelectric cooler, and/or any other suitable device, may be used to lower the elevated temperature of one of the support assembly, the assay device, and sample. In still further embodiments of the invention, the assay device may be cooled by rinse reagents that are applied subsequent to the heating step 23 in order to provide the necessary cooling.

In one exemplary embodiment of the invention, excess buffer agent, if any, is removed 27 following the cooling step 25. Any suitable process for removing excess buffer agent may be used in the inventive device. Non-limiting examples of processes that can be used to remove excess buffer may include washing, aspiration, gravity-inducement, displacement using a stream of air or any other fluid, and any other suitable processes or combinations thereof.

The assay device may also be subjected to an optional rinse step 29. In an embodiment of the invention, a fluid, such as deionized water, is used in the rinse step 29 as the rinsing solution. In yet another embodiment of the invention, a specially prepared rinsing solution is used in the rinse step 29. In even yet another embodiment of the invention, a combination of deionized water and a specially prepared rinsing solution is used in the rinse step 29. In another embodiment of the invention, the excess buffer removal step 27 and rinsing step 29 may carried out substantially simultaneously.

In the exemplary embodiment of FIG. 2, the staining module 30 comprises a reagent addition step 32 where one or more reagents are added to the assay device. Following reagent addition 32, the assay device undergoes a defined heating period or procedure 34. Following the heating procedure 34, excess reagent, if any, is removed 36 from the assay device. Any process known in the art for removing excess reagent may be used in the inventive device. Non-limiting examples of processes that can be used to remove excess reagent can include any of washing, aspiration, gravity-inducement, displacement using a stream of air or any other fluid, and any combination thereof. The assay device may also be subjected to a rinse step 38. In an embodiment of the invention, water, in some instances, deionized water, is used in the rinse step 38 as the rinsing solution. In yet another embodiment of the invention, a specially prepared rinse solution is used in the rinse step 38. In even yet another embodiment of the invention, a combination of deionized water and a specially prepared rinsing solution is used in the rinse step 38. In another embodiment of the invention, the excess reagent removal step 36 and rinsing step 38 are carried out substantially simultaneously.

In certain embodiments of the invention, the staining module may be configured to perform one or more reagent addition sequences that apply the same reagent(s) to each of the assay device(s). The reagents may be applied substantially simultaneously, in series, or in any combinations thereof to the various assay devices, with each assay device receiving the reagent(s) in a manner consistent with the other assay devices. In such embodiments, each assay device may be subjected to another heating period 34 following each of the defined reagent addition sequences. However, it may or may not be necessary to perform excess reagent removal 36 and rinsing 38 after each reagent addition sequence. Nonetheless, excess reagent removal 36 and rinsing 38 may be performed following the heating period 34 for the last reagent addition sequence.

The various modules as shown in the schematic of FIG. 1 and the illustration of FIG. 2 are merely exemplary or illustrative of certain embodiments of the invention and should not be considered as limiting. A person skilled in the art, having the benefit of this disclosure, would understand that any number of configurations of modules in the footprint of the inventive device is possible. Indeed, in certain embodiments of the invention, the modules may be placed in more than one footprint. All such configurations are intended to be part of this disclosure.

FIG. 3 is a perspective view, according to one embodiment of the invention, of a sample preparation device. FIG. 4 is a side view illustrating one embodiment of the sample preparation device shown in the perspective view of FIG. 3. FIG. 5 is a section view taken along the V-V line of FIG. 4 illustrating one embodiment of the sample preparation device shown in the perspective view of FIG. 3. In this exemplary embodiment, the structure of the sample preparation device 100 is defined by a base 101, a hood 102, and support members—a left support member 103 and a right support member 104.

The base 101, hood 102, left support member 103, and right support member 104 cooperate, for example, to define the structure housing the modules comprising the sample preparation device 100. Of course, as shown in FIG. 3, and as further discussed herein, the modules and other devices of the sample preparation device 100 may be secured to any of the base 101, the hood 102, the left support member 103, and the right support member 104. One end of each of the left support member 103 and right support member 104 is secured to the base 101 and another distally opposite end of each of the left support member 103 and the right support member 104 is secured to the hood 102 allowing the hood 102 to overhang at least a portion of the area defined by the base 101. A sample rack 106 may hold a plurality of sample vials 116, which each may contain a sample to be further processed using the sample preparation device 100. The sample tray 106 with a plurality of sample vials 116 may be manually placed in the sample preparation device 100.

Another embodiment of a sample preparation device 400 is shown in FIGS. 24-28. The sample preparation device 400 is similar to that described above. The sample preparation device 400 includes a drawer 402 for receiving reagent kits 404, tip cartridges or racks 406, and sample tube holders 408. The drawer 402 is configured to be slidably withdrawn from or advanced into the sample preparation device 400 by a technician for easier access to each of the components. The sample preparation device 400 also includes an RFID reader/writer 410 as described above for reading/writing to each of the reagent kits 404. FIG. 28 illustrates one exemplary embodiment of a sample preparation device 400 wherein seven reagent kits 404, two tip racks 406, and four sample tube holders 408 (each tube holder including 12 sample tubes) are used, although one would recognize that different numbers of each component could be utilized for a particular system.

As described in further detail below, each of the slides 118 may be positioned on a support plate 412, wherein FIGS. 24 and 25 show that there are four support plates each configured to receive 12 slides 118 corresponding to the number of tubes 116 within the tube holder 408, although it is understood that any number of tubes, tube holders, slides, and support plates may be employed if desired. According to one embodiment, each support plate 412 is configured to slide into and out of the sample preparation device 100 via a drawer 418, allowing for easier access to the slides. Moreover, the sample preparation device 400 includes a series of doors 414 enclosing each of the components to create a closed system, such as a door corresponding to the drawer 402 and each of support plates 412. In one aspect which is also described in greater detail below, moving a door 414 associated with a respect support plate 412 correspondingly moves a heater plate 416 from a spaced apart location with respect to the support plate into direct engagement with the support plate when the door is closed for heating by a heating device 420.

The embodiment illustrated in FIG. 3 shows a control system 108. Without intending to be limiting, the control system 108, which may be used to automatically control the sequencing of steps, for example, such as those shown in FIG. 2, needed to prepare an assay device with a sample. As shown, the control system 108 may include a monitor for supplying information to an operator. However, the control system 108 may also include a processor, a memory, a bus, a storage device, and at least one input/output device. A control system 108 may additionally comprise a keyboard and/or a mouse in order for the operator and/or programmer to interface with the sample preparation device.

In embodiments of the invention, the control system 108 may be configured to automatically control any or all of the operations, or combinations of operations, of the sample preparation device 100. The control system 108 may additionally provide sample tracking using, for example, an ID assigned to a sample. The control system 108 may also alert an operator through at least one of a message displayed on the monitor, a visual alarm on an alarm panel (not shown), and an audible alarm as to a condition of the system. In certain embodiments of the invention, the control system 108 may be interfaced to a network and send a message to an operator via an e-mail, text messaging, or any other remote communications device. In a certain embodiment of the invention, the control system 108 also comprises a remote monitoring device to allow an operator to remotely gain access to information from the control system 108.

In one embodiment of the invention, the control system 108 may be configured to perform diagnostic and troubleshooting procedures in order to resolve problems that may occur in the system. In certain embodiments of the invention, the control system 108 can merely report these problems to an operator through, for example, one of the communication channels and/or devices discussed above. In other embodiments of the invention, the control system 108 will have the capability to resolve and/or correct a problem that may occur in the device. In another embodiment of the invention, the control system 108 will guide an operator through troubleshooting procedures in an effort to resolve a problem that may have occurred in the system. In some embodiments of the invention, the control system 108 may be configured to coordinate the processing of assays using any number of steps and/or procedures specific to a particular sample. In some instances, the control system 108 is configured to substantially simultaneously coordinate the processing of assays using any number of steps and/or procedures specific to a particular sample.

Certain embodiments of the invention may provide a sample identification module. The sample identification module will be selected based upon the indicia of reference or other device for identifying the sample that is consigned by the system. The sample identification module can be any suitable type of scanning system including, but not limited to, a barcode scanner, an electronic magnetic scanner, a RF antenna transceiver, or a microprocessor based tracking system. Of course the indicia of reference or other device for identifying the sample that is implemented by the system must be commensurate with the type of scanner being employed. In coordination with at least one sample identification module, if implemented, the control system 108 may further comprise a tracking system for providing chain of custody information for the processed samples. In one embodiment of the invention, the control system may be interfaced with a laboratory information system (LIMS), which can be useful, for example, in reporting the status of a sample.

The sample or a portion of a sample contained in a sample vial 116 that has been provided to the sample preparation device 100, may be transferred to the assay device(s) by a transfer assembly 110. In this exemplary embodiment, the assay device is a slide 118; however, the assay device may be any device known in the art used for holding a sample, including a cassette, a slide (including microslides), a Petri dish, a tube, a bottle, a plate including multi-plate assemblies, a cup, a septum, a pipette, a syringe, a titer (including microtiters), a capillary array, a tray, a gel pack, a swab, an applicator, any fibrous media, and any combination thereof. Indeed, an assay device may be any media, device, apparatus, or support that is capable of receiving a sample and allows that sample to undergo further analysis.

A non-limiting example of a transfer assembly may include a combination of an aspiration device for removing the sample from one sample container and a dispensing device for injecting the sample into another sample container. While in this exemplary embodiment of the invention, the sample is contained in a sample vial 116, the sample to be processed may be held by another type of collection device, such as a swab, broom-type sampling device, or brush. Of course other types of transfer assemblies known in the art may be more suitable for transferring the sample contained on these types of devices to the slide. In some instances, to the extent possible, the choice of transfer assembly 110 will be such that the amount of human contact needed with the sample is minimized, if not eliminated entirely, in order to reduce the risk of sample contamination.

In some instances, an aspiration and dispensing arm 111 of the transfer assembly 110 is equipped with a tip 112. The aspiration and dispensing arm 111 may be configured to releasably engage a tip 112 from a tip dispenser 114 when the aspiration and dispensing arm is positioned over and brought into engagement with such a tip 112 in the tip dispenser 114. Once a sample has been aspirated from a sample vial 116 via the tip 112 and dispensed onto a slide 118, the transfer assembly 112 positions the aspiration and dispensing arm 111 over a tip discard tray 122, and the used tip 112 is released by the aspiration and dispensing arm 111 into the tip discard tray 122.

In some instances, the transfer assembly 110 is moveably attached to a conveyor and/or cam system (or other suitable translational device or movement device) affixed to a lower surface of the hood 102 to enable the transfer assembly 110 to be moved in a horizontal direction. The transfer assembly 110 may be capable of moving vertically in an upwardly and downwardly direction and, in some instances, may be rotatably attached to the conveyor and/or cam system or even to the body of the transfer assembly 110. As such, in some embodiments of the invention, an aspiration and dispensing arm 111 of the transfer assembly 110 may be moved to any desired position with respect to the sample preparation device 100. For example, the transfer assembly 110 can be positioned to allow the aspiration and dispensing arm 111 to be positioned over a tip 112 in the tip cartridge 114. The aspiration and dispensing arm 111 can be moved in a downwardly direction to releasably engage the tip 112 and then in an upwardly direction to retrieve the tip 112. The transfer assembly 110 can then position the aspiration and dispensing arm 111 with a tip 112 over a sample vial 116 and move in a downwardly direction until a portion of the tip 112 is disposed in the sample. At least a portion of the sample from the sample vial 116 is aspirated into the tip 112. The transfer assembly 110 can also move the aspiration and dispensing arm 111 with tip 112 containing at least a portion of the sample, in an upwardly direction and relocate the aspiration and dispensing arm 111 until it is aligned with a slide 118 that is to receive the sample portion. The transfer assembly 110 may then dispense the sample portion contained within the tip 112 onto the surface of the slide 118. The transfer assembly 112 may then position the aspiration and dispensing arm 111 over the tip discard tray 122 where the used tip 112 is released and discarded.

The exemplary embodiment of FIG. 3 shows a transfer assembly 110 having a plurality of aspiration and dispensing arms 111. In some instances, a transfer assembly 110 having a plurality of aspiration and dispensing arms 111 may have the aspiration and dispensing arms 111 positioned such that when transfer assembly is positioned over a tip cartridge 114, each of the aspiration and dispensing arms 111 will be suitably aligned over a tip 112. In other instances, a transfer assembly 110 having a plurality of aspiration and dispensing arms 111 may have the aspiration and dispensing arms positioned 111 such that when the transfer assembly 110 is positioned over a sample tray 106 holding a plurality of sample vials 116, each of the tips 112 on the aspiration and dispensing arms 111 will be suitably aligned over a sample vial. Moreover, a transfer assembly 110 having a plurality of aspiration and dispensing arms 111 may have the aspiration and dispensing arms positioned 111 such that when the transfer assembly 110 is positioned over a support plate holding the same number of slides 118, each of the tips 112 on the aspiration and dispensing arms 111 will be suitably aligned over a slide. Such embodiments allow the transfer assembly 110 to aspirate and then dispense a plurality of samples simultaneously.

In another embodiment of the invention, the transfer assembly 110 may use a pipette to transfer at least a portion of a sample contained, for example, in a sample vial onto an assay device. In some embodiments of the invention, the transfer assembly 110 may use an automated pipette transfer assembly to transfer at least a portion of a sample to an assay device. In certain embodiments of the invention, the transfer assembly 110 may be automated and, in addition to sample transfer, may also implement automated sample mixing in the sample container and layering of the sample onto an assay device. In some instances, the transfer assembly 110 may be configured to automatically mix, transfer, and layer a desired amount of a sample onto an assay device. In some instances, any pipette used in a transfer assembly 110, whether the assembly is fully manual, in part manual, or automated, is disposable in order to minimize or eliminate the possibility of sample contamination. One non-limiting example of a commercial sample transfer module that may be used in certain embodiments of the invention include the BD™ High Throughput Sampler manufactured by Becton Dickinson of Franklin Lakes, N.J.

The slides 118 used by the sample preparation device 100 may be held in a slide cartridge 120. Further, the sample preparation device 100 may include a number dispensers configured to dispense solutions used as the inventive system processes assays. The exemplary embodiment of FIG. 3 also shows a buffer rinse solution dispenser 126, an alcohol blend dispenser 128, and a deionized water dispenser 130, wherein each of the dispensers may be capable of automatically positioning itself above each of the slides where its corresponding solution will be required. Various types of buffers, reagents, and/or solutions may be used in the slide preparation process. In embodiments of the invention where the sample preparation device 100 is used to prepare immunocytochemistry assays, the sample preparation device may also be equipped with an epitope retrieval solution dispenser 124 that disposes an appropriate solution substantially across the sample disposed on the surface of each of the slides 118 being processed by the sample preparation device 100.

In those circumstances when the preparation of assays requires a greater number of reagents or in those circumstances when the sample preparation device will be successively processing a multiplicity of assay types, additional reagents may be supplied in a reagent kit 160. The transfer assembly 110, using aspiration and dispensing techniques similar to those described herein, will aspirate the needed reagent from the reagent kit 160 and dispose the appropriate reagent on the slide 118 whose preparation requires such reagent. The ability to configure dispensers to dispense certain solutions and to process an assay using reagents from the reagent kit 160 provides the sample preparation device 100 with its capability of preparing any number of sample protocols and preparing such protocols substantially simultaneously if required.

According to one embodiment, each reagent kit 160, such as a detection and/or control kit, may include an RFID tag that includes various types of information, such as kit type, assay capability, lot number, expiration date (i.e., "unopened"), number of tests remaining in the kit, date first used, expiration data (i.e., "opened"). When the kits are placed in the sample preparation device 100 and the sample holder or rack drawer is secured, an RFID reader 410 reads the information on the kits. The RFID reader is configured to read the RFID tags in sequence as the drawer is advanced into the sample preparation device 100. If the expiration dates are past due, the process will pause, and an operator may be alerted. In addition, the process will only run on assays that can be used for the kits ("assay capability"). In there are an insufficient number of tests remaining in the kits, the process will pause and alert the operator of the error. The sample preparation device 100 is configured to update the number of tests remaining for each kit at the end of an assay run based on the number of samples successfully run or the stage of the process if the assay was interrupted during the run. According to one embodiment, the RFID reader 410 also has writing capabilities and is configured to write updated information to the RFID tags, such as number of tests remaining and date of first use.

According to one embodiment, the sample preparation device 100 may employ a level detection system using conductive pipette tips, such as a RSP 9000 system manufactured by Tecan Group Ltd. The liquid level detection system is configured to confirm the number of tests remaining in case of a reagent spill or if the operator tries to "re-load" reagents. The pipette tips only submerge as low as needed into the reagents to prevent overflowing during processing, and the sample preparation device 100 is configured to detect if no reagent or sample is present. As such, the level detection system may be used as a physical confirmation of the RFID information associated with the reagent kits.

In one embodiment, the sample preparation device 100 is configured to determine the presence or absence of a conductive tip in a tip cartridge or rack. For example, the sample preparation device 100 may utilize a level detection system having a conductive tip that is able to detect a tip in all four corners of a tip rack (e.g., by touching the outside surfaces of the tips in the tip rack), it can assume that there is at least one full rack of tips, confirming an adequate supply of tips to perform an assay run. The sample preparation device 100 may contain two tip racks for this purpose.

Moreover, in an additional aspect, the sample preparation device 100 includes a separate waste "bath" receptacle 422 for each of the bulk reagent dispense and aspiration bundle sets 424. These baths are essentially individual cups into which the sample preparation device 100 primes reagents and then vacuums them back out. This design allows the diversion of reagents during the vacuuming aspiration step via a downstream waste diverter.

According to an additional embodiment, the reagent waste is vacuumed from the waste bath receptacles 422 and delivered to waste containers 426 via a vacuum 428. A diverter valve 430 used in conjunction with a manifold may be used to divert waste from a particular receptacle to a specific waste container. For example, where four waste receptacles 422 are used, the waste may be drawn into the manifold, while the diverter directs the waste to a particular waste container. When vacuuming the waste from the waste receptacles, the positive pressure side of the vacuum is usually open to air allowing volatile organics to escape into the atmosphere. For instance, reagents may be alcohol based, allowing alcohols such as methane and isopropyl to vaporize and escape into the atmosphere resulting from low-pressure distillation, which may create a safety hazard and subject technicians to bothersome odors and noise. In order to address this problem, a scrubbing muffler 432 may be utilized that includes an air diffuser 434 and a water bottle 436, as shown in FIGS. 29 and 30. The water bottle 436 contains water 438, and the exhaust is directed into the water bottle via an inlet 440 defined in a cap 442 and through an air diffuser 434, wherein the air diffuser is configured to diffuse the incoming alcohol vapor into the water such that the water absorbs the alcohol thereby reducing or eliminating the release of vapor into the atmosphere. The water bottle 436 also includes an outlet 444 for exhausting air. The scrubbing muffler 432 may also reduce noise resulting from vacuuming the reagent.

The sample preparation device 100 can dispense a known volume of a specific reagent into the waste "bath" receptacles 422. The conductive tip can measure the "Z-Height" value of each waste bath and determine if the dispensed reagent levels are acceptable (overall and bath-to-bath) as compared to the expected "Z-Height" level based on the volume dispensed. The sample preparation device 100 may be further configured to vacuum the dispensed reagent in the above step for a brief period of time, however insufficient time to completely evacuate the entire waste bath. The conductive tip can measure the "Z-Height" value of each waste bath and determine if the remaining reagent levels are acceptable (overall and bath-to-bath) as compared to the expected "Z-Height" level based on the expected aspiration rate. Thus, the sample preparation device 100 may be used to confirm that the fluidics and related components are operating properly before loading samples and reagents onto the slides.

According to another embodiment, the sample preparation device 100 utilizes techniques to determine the liquid level of the bulk reagents and the vacuumed waste. For instance, conductive strips, float switches, optical means, or other techniques may be used for such purposes. For example, each bulk reagent container 424 may sit on a load cell and depending on the weight of the container, it may be determined whether there is a sufficient amount of reagent to run the tests. If there is insufficient bulk reagent to perform the number of tests required, the process will pause and alert the operator of the error. Similarly, the waste containers 426 may employ load cells to determine whether there is sufficient head space in the containers based on the weight thereof.

Furthermore, the sample preparation device 100 may include different sensors to determine whether proper placement or alignment of various components has been achieved. For example, sensors may be employed to determine whether access doors 414 are closed, sample racks are properly positioned, and/or solenoids have been activated.

The sample preparation device 100 is also capable of processing a plurality of slides 118 simultaneously. The plurality of slides may be processed substantially simultaneously according to the steps required for a particular type of assay protocol. In the exemplary embodiment shown in FIG. 3, the slides may be positioned on one or more support devices, such as support plates—a first support plate 132, a second support plate 134, a third support plate 136, and a fourth support plate 138 being shown as an example. Each support plate is held in place by a support bracket 140. The exemplary embodiment shows four slides 118 are aligned substantially parallel to each other across a support plate, though any number of slides 118 may be aligned across the support plate. Indeed, an embodiment of the invention only allows one slide 118 to be supported by a support plate. Further, one or more slides 118 may be supported along the support plate such that the slides supported by the support plate form a matrix.

Certain assay protocols capable of being prepared by the sample preparation device 100 require that heat be applied to the assay device(s)/sample(s) over a specified period of time, during the processing cycle. As such, the sample preparation device 100 may be equipped with one or more heating devices—i.e., a first heating device 142, a second heating device 144, a third heating device 146, and a fourth heating device 148. In some instances, one or more heating devices may be provided, wherein the heating device(s) are configured to operably engage each support plate and/or the assay device(s) supported thereby. In an embodiment of the invention, the heating device may be operably engaged with a support device, such as the support plates 132-138, to provide a desired rate of heat transfer and/or a requisite amount of heat to a slide 118. Further, each heating device may have a separate and discrete temperature controller—a first temperature controller 152, a second temperature controller 154, a third temperature controller 156, and a fourth temperature controller 158—affixed, in this exemplary embodiment, to the right support member 103. The temperature controllers are used to maintain a desired temperature of each of their respective support plates. In one instance, it may be desirable to maintain a desired temperature at a contact location between the support plate and the assay device(s). In one embodiment of the invention, one or more thermocouples affixed to each of the support plates (not shown) may provide temperature feedback to each of the respective controllers in order to maintain a desired temperature at the support plate. In one embodiment of the invention, the heating devices 142-148 are resistive heaters each individually affixed to a respective support plate 132-138, and configured to heat the corresponding support plate 132-138 and any slide 118 removably engaged with said plate to substantially the same temperature. That is, desirably, the design of the heating system is such that there is substantially no temperature gradient between a support plate 132-138, the engagement between the support plate 132-138 and a slide 118, and the slide 118.

According to another aspect of the invention, the heating devices 142-148 may be used to apply heat at other at other points along the process of preparing an assay device. Any of the heating devices disclosed herein may be used for the heating devices 142-148. Moreover, a person having ordinary skill in the art having the benefit of this disclosure, may envisage other configurations of the heating device with such other configurations intending to be part of this disclosure.

According to certain aspects of the invention, the contact between the surface of the heating device and the opposing surface where heat is to be supplied, which can include, but is not limited to, for example, the surface of the carriage, the surface of the assay device, and the surface of the support plate, may be important in ensuring the amount of heat supplied to the opposing surface is substantially consistent. For example, in certain circumstances, a failure to achieve a consistent amount of heat transfer may result in uneven temperature profiles that can affect the repeatability of results that are achieved in processing the assay devices. The term "compliance" is used herein to reference the contact between the surface of the heating device and the opposing surface where heat is to be supplied. Compliance represents many facets of the contact that is achieved between two surfaces. For example, compliance includes, but is not limited to, the extent of surface contact achieved between the surfaces, the amount of pressure existing at the point or points of contact between the surfaces, and any combination thereof. An aspect of the invention provides a heating module assembly, for receiving, supporting, and heating the assays and to interact with the sample preparation device 100. In some embodiments of the invention, the configuration of the heating module assembly and the heating devices will be such that the compliance among each heating device and the respective opposing surface is substantially the same.

According to one aspect of the invention, compliance may be "passively" achieved, for example, through a carriage and/or carriage assembly associated with the heating module assembly. In certain embodiments of the invention, compliance may in part be achieved through the installation of a carriage and/or carriage assembly into the heating module assembly, and full compliance may be achieved by using some device and/or functionality to achieve a greater degree of compliance with the one or more heating devices. Partial compliance may be achieved, for example, when the desired degree of surface contact between the surface of the heating device and the opposing surface where heat is to be supplied is not achieved. However, the full extent of desired compliance, e.g., sometimes achieved when the contact between the surface of the heating device and the opposing surface is such that the rate of heat transfer to the opposing surface is relatively fast and the amount of heat applied across the opposing surface is substantially consistent, may be achieved through the use of perhaps a locking mechanism or some other mechanism to more fully engage the carriage and/or carriage assembly with one or more heating devices. According to other aspects of the invention, compliance is achieved through an additional action or actions taken on the carriage, carriage assembly, heating module assembly, and combinations thereof, such as, for example, through the use of a supplemental device to enhance the contact that is achieved between the carriage and/or carriage assembly and the assay device, of which some exemplary approaches are more fully disclosed herein.

In an embodiment of the invention, each support plate is equipped with a heating module assembly having one or more heating devices in communication with, for example, a controller having temperature feedback, with such temperature feedback provided through any temperature indicator known in the art. In certain embodiments of the invention, temperature feedback to the controller indicating the temperature of the support plate or even the temperature of an assay device on a support plate may be provided by the use of a thermocouple.

FIG. 6 is a perspective view of a heating module assembly for a sample preparation device, according to one aspect of the present invention. The heating module assembly 200 is defined by a housing 202, which may include slots 196a, 196b for receiving and positioning of a carriage assembly 170 installed into the heating module assembly 200, as further described herein. In this exemplary embodiment, the carriage 204 is configured, as further described herein, to receive a support device such as a support plate 132, which is further configured to support assay devices. In other embodiments, the carriage itself may be designed to hold a plurality of assay devices 118 without the use of a support plate.

FIG. 7 is a perspective view of a carriage assembly of a heating module assembly for a sample preparation device, according to one aspect of the present invention. The carriage assembly 170 is defined by a carriage 204 that may be laterally positioned within the housing 202 by the use of one or more extension arms 170a, 170b extending away from the forward part of a sidewall 188. In this exemplary embodiment, the carriage 204 has opposed shoulders 172a, 172b that provides support for a support plate 132 by laterally engaging opposing sides of said plate. At least two legs 174a, 174b are provided for each shoulder 172a, 172b, allowing said shoulders to become demountably or affixedly engaged with and supported by a frame 176 of the carriage assembly 170. Optionally, in certain embodiments, the legs 174a, 174b may be designed to act as compressive struts or spring assemblies allowing a support plate 132 to be evenly biased relative to its position in the heater module assembly 200 with respect to the frame in the event of an uneven weight distribution along the support plate 132.

The base of the frame 176 defines at least one cavity 178a, 178b allowing various wires, cables, and the like to be directed into the carriage assembly 170. For example, such wires, cables, and the like may be for the purpose of supplying electricity to a heating device (not shown), wires leading to a thermocouple to measure any temperature throughout the heating module assembly 200, and any combination thereof. The at least one cavity 178a, 178b, in certain embodiments of the invention, may also allow for faster heat dissipation from the carriage assembly 170, for example, by allowing heat to become more easily removed from a compartment 180, in order to ensure at least one of more even heat distribution, quicker cooldown when heat is removed, and combinations thereof. The frame 176 may have one or more compartments 180 formed by the use of dividers 182a, 182b. Such compartments 180 may serve, for example, as a housing for a heating device (not shown). In certain embodiments of the invention, at least one compartment may be provided for the purpose of improving the distribution of heat throughout the carriage assembly 170 by, for example, by acting as a heat source having a substantially uniform temperature wherein the rate of heat transfer is substantially constant and uniform across the carriage assembly 170. An even distribution of heat throughout the carriage assembly 170 will, among other things, assist with providing a more even temperature distribution across the support plate 132 and a greater repeatability of results achieved from the prepared assays.

A carriage support chassis 184 engages and becomes substantially aligned with the outer wall of the frame 176 and runs substantially parallel with shoulder 172b. One or more nubs 186a, 186b are secured to the carriage support chassis 184 and axially extend therefrom for purposes of slidably engaging the upper edge of a sidewall 188 that is longitudinally disposed along a wall of housing 202. The sidewall 188 has one or more, preferably two, channels 190a, 190b, allowing the carriage 204 to become seated in the housing relative to the position of the heating device as the one or more nubs 186a, 186b are allowed to traverse the contours of the channels 190a, 190b. Guide pins 192a, 192b extend from the bores 194a, 194b in the housing 202. Guide pins 192a, 192b engage slots 196a, 196b to facilitate horizontal positioning of the carriage assembly 170 with respect to the heating device. In certain embodiments of the invention, the final vertical positioning of the carriage assembly 170 in the housing 202 achieved by establishing a proper positioning of nubs 186a, 186b on the channels 190a, 190b, and horizontal positioning of the carriage assembly 170 in the housing 202 achieved by the position of the guide pins 192a, 192b in slots 196, 196b may be important to achieving the desired compliance between the heating device and opposing surface to be heated.

The carriage assembly 170 may become operably engaged and secured in the heating module assembly 200 though the use of one or more securing devices 198, such as, for example, with the use of a turn screw or a thumbscrew. Though not shown, but as can be envisioned based on the diagram in FIG. 7, the opposite side of the carriage assembly 170 also comprises a chassis 184; nubs 186a, 186b; a sidewall 188; channels 190a, 190b; pins 192a, 192b; and slots 196a, 196b.

FIG. 8 is a perspective view showing a heating module assembly in multiple gradated forms of assembly for a sample preparation device, according to an aspect of the present invention for a sample preparation device, according to an aspect of the present invention. The exemplary embodiment illustrated in FIG. 8 is representative of an embodiment of the invention where a single heater module 142 corresponds to each heating module assembly 200. Further to this exemplary embodiment, the heater rack 201 comprises four heating module assemblies 200, the heating module assemblies each having a corresponding carriage assembly 170 and support plate 132 each capable of supporting one or more assay devices. As can be envisaged by a person having ordinary skill in the art, the heater rack 201 may be configured to have any number of heating module assemblies 200. The functionality of the heater module assembly 200 and carriage assembly 170 of FIG. 8 are further described above. Additionally, however, the frame 176 is also defined by another opening 179 through which wires, cables, and the like may be directed into the carriage assembly 170. Also shown is a channel 181 through which such wires, cables, and/or the like may be directed allowing for heating devices to be easily disconnected and removed and replaced and reconnected in the heating module assembly 200.

In other embodiments of the invention, each of the slide-contact positions on a support plate (i.e., where a slide 118 is to be positioned) is equipped with its own heating device, in communication with, for example, a controller having thermocouple feedback. For example, such an aspect of the invention provides a heating module assembly 200, for receiving, supporting, and heating the slides 118 and to interact with the sample preparation device 100. FIG. 9 is a side view of a heating module assembly wherein compliance between the carriage and a heating device is achieved, according to such an embodiment, while FIG. 10 is a perspective view of such a heating module assembly. The heating module assembly 200 may be defined by an assembly housing 202 and a carriage 204. The carriage 204 is configured to receive a support device, such as a support plate 203, configured to support the slides 118, and is movably affixed to the assembly housing 202 at connections 206, 207. More particularly, the carriage 204 is rotatably engaged with the assembly housing 202 about connections 206, 207, and securable in a desired disposition with respect to the assembly housing 202 through interaction with a latch 208 and retaining mechanism 211. More particularly, the carriage 204 may comprise opposing channels 205a, 205b for slidably receiving the support plate 203. The support plate 203 may include a locating pin 203a that engages and extends through a slot 210a defined by a receiving member 210 engaged with one of the channels (i.e., 205b). The locating pin 203a engages the rotatable retaining mechanism 211 upon insertion into the slot 210a such that the support plate 203 is prevented from exiting the channels 205a, 205b, without positive pivoting of the retaining mechanism 211 away from the locating pin 203a to allow the locating pin 203a to exit the slot 210a.

A heating module 212 is slidably inserted into the assembly housing 202 following a track 214, wherein the heating module 212 is desirably secured in a selected position within the assembly housing 202. The heating module 212 further comprises a plurality of heating devices 216. In one embodiment of the invention, a heating device 216 may be provided for and, optionally, is in compliance with each position that a slide 118 may occupy and interact with the support plate 203 (i.e., in an x by y matrix). Thus, as further described herein, the heating device(s) 216 can be configured and positioned relative to the slide 118 (i.e., to extend through the support plate 203 so as to be in compliance with the slide 118) such that a consistent rate of heat transfer and/or a desired amount of heat can be provided to the slide 118, such that all slides 118 are heated to substantially the same temperature. In one instance, the heating devices 216 can provide the assay protocol-dependent, requisite temperature(s) and/or temperature profiles with respect to the slides 118, as controlled by one or more controllers (not shown) In the exemplary embodiment of FIGS. 9 and 10, the heating module 212 may be released from the assembly housing 202, as necessary or desired.

The assembly housing 202 having the heating module 212 installed therein may then be installed in a register position with respect to the sample preparation device 100 through, for example, an appropriate engagement with the base 101. Once installed in the sample preparation device 100, appropriate connections (i.e., electrical connections) may be established to the heating module 212 for powering the heating devices 216. In this manner, the sample preparation device 100 may be selectively configured for processing appropriate amounts of samples as necessary or desired (see, e.g., FIG. 11). Once the desired number of assembly housings 202 is engaged with the sample preparation device 100, a suitable support device 203 holding/supporting an appropriate number of assay devices (slides) 118 may be inserted into each assembly housing 202, as previously disclosed. The respective support plate 203 may then be urged toward the latch 208 and into a sample preparation initiation position with respect to the heating module 212. That is, by urging the support plate 203 toward the latch 208, the pivotable connections 206, 207 causes the carriage 204 (and thus the support plate 203) to also move toward the heating module 212 (i.e., such that the carriage 204 orbits around the connections 206, 207) such that the heating devices 216 align with and are received by corresponding pass-through channels 203b defined by the support plate 203. The latch member 208 (which may be appropriately biased or "spring loaded") is thus caused to interact with the carriage 204 (i.e., one of the channels 205a, 205b) such that the carriage 204 and support plate 203 are maintained in compliance with the heating module 212 (the sample preparation initiation position). The latch member 208 may be released from securement of the carriage 204/support plate 203 through actuation of a release member 218. The release member 218 may also be appropriately biased (i.e., to provide a "push button" form of operation). Further, the carriage 204 and/or the connections 206, 207 may also be appropriately biased such that the carriage 204 is normally biased away from the sample preparation initiation position.

In some instances, the ability to insert and later remove the heating module 212 from the assembly housing 202 desirably allows the workspace to more conveniently be cleaned and allows the heating module 212 to be easily connected to an electrical supply. Further, such a heating module assembly 200 may also facilitate a "single action" engagement of the support plate 203 (and assay devices 118 supported thereby) with the sample preparation device 100 since, for instance, an operator merely needs to slide the support plate 203 into the channels 205a, 205b until the carriage 204 interacts with the latch 208 In doing so, the heating module assembly 200 is configured such that the slides 118 supported by the support plate 203 each individually and directly come in compliance with a corresponding heating device 216 associated with the heating module 212.

In another aspect of the invention, the heating module assembly 200 is provided with another receiving mechanism for receiving the support plate 203 and reversibly bringing the support plate 203 into compliance with the heating module 212. FIG. 12 illustrates a side view and FIG. 13 provides a perspective view of a heating module assembly implementing a door member/linkage mechanism. In this exemplary embodiment, a first end of a door member 220, is pivotally attached to a vertical extension 204a of the carriage 204 at a pivot point 222, while an opposing second end of the door member 220 is movable about the pivot point 222. An extension of the first end of the door member 220 extends from the pivot point 222 away from the second end of the door member 220. The first end extension may, in turn, be operably engaged with a linkage (not shown) at 223, the linkage extending from therefrom into engagement with the assembly housing 202. The carriage 204, as previously, includes opposing channels (not shown) for receiving the support plate 203. The carriage 204 is vertically movable with respect to the assembly housing 202, for example, via guide pins 226a, 226b engaged with corresponding slots 227a, 227b defined by the assembly housing 202. In this manner, pivoting of the second end of the door member 220 away from the assembly housing 202 causes the first end extension to actuate the linkage which, in turn, interacts with the assembly housing 202 to move the guide pins 226a, 226b (and thus the carriage 204/support plate 203) toward the upper portions of the corresponding slots 227a, 227b. In doing so, the vertical movement of the carriage 204 and support plate 203 supported thereby, removes the support plate 203 and slides 118 supported thereby from compliance with the heating devices 216 of the heating module 212. Conversely, rotating the second end of the door member 220 toward the assembly housing 202 retracts the linkage from engagement with the assembly housing 202 and thus causes the carriage 204/support plate 203 to be lowered with respect to the slots 227a, 227b and into compliance with the heating devices 216 of the heating module 212. Appropriate interaction between the support plate 203 and heating module 212 may be facilitated, for example, by one or more alignment members 228 operably engaged with one of the heating module 212 and the support plate 203. Accordingly, "opening" the door member 220 allows the support plate 203 (and slides 118 carried and supported thereby) to be inserted into (or removed from) the carriage 204. Further, "closing" the door member 220 causes the support plate 203/slides 118 to be lowered into compliance with the heating module 212, while preventing the support plate 203 from being removed. Accidental release or removal of the heater module 212 from the assembly housing 202 may be prevented, for example, by implementing a securing device 230 such as, for example, a thumbscrew capable of being operably engaged between the heater module 212 and the assembly housing 202. In this regard, FIG. 14 is a perspective view of a plurality of heating module assemblies 200, each configured with a door member 220/linkage mechanism, and mounted in a sample preparation device 100 according to one embodiment of the invention.

In another aspect of the invention, the heating module assembly 200 may be equipped with another receiving mechanism for receiving the support plate 203 and reversibly bringing the support plate 203 into compliance with the heating module 212. FIG. 15 is a side view of a heating module assembly equipped with an actuator handle 240. The actuator handle 240 may be configured to engage the carriage 204, for example, via a cam mechanism 241. In one embodiment, the actuator handle 240 is rotatable about a common rotation point 243 with respect to the cam mechanism 241. As such, in a first position of the actuator handle 240 (i.e., as shown in FIG. 15), the carriage 204 is raised with respect to the assembly housing 202 so as to allow the support plate 203 (supporting the slides 118) to be inserted into the carriage 204. Upon insertion of the support plate 203, rotation of the actuator handle 240 to a second position (i.e., clockwise with respect to the first position, as shown in FIG. 15), causes the cam mechanism 241 to move the support plate 203, and the slides 118 supported thereby, vertically downward into compliance with the heating elements 216 of the heating module 212. FIG. 16 further provides a perspective view of a heating module assembly with an actuator handle/cam mechanism mounted in sample preparation device 100.

Another aspect of the invention provides a heating device 216 as implemented, for example, in conjunction with the various embodiments of a heating module 212 previously described. While multiple embodiments of heating devices are disclosed, still other embodiments of the heating device will become apparent to those skilled in the art having the benefit of these exemplary embodiments. In some embodiments of the invention, the slides (assay devices) 118 are brought into compliance with the individual corresponding heating devices 216 by moving the support plate 203 into compliance with the heating module 212 by various mechanisms. However, in order to heat each of the assay devices 118 to substantially the same temperature (as accomplished through direct contact between the individual heating devices 216 and the corresponding assay devices 118), substantially uniform pressure/contact between the assay devices 118 and heating devices 216 is desirable. Such uniform pressure/contact may sometimes not be readily achieved with the mechanisms bringing the assay devices 118 into contact with the heating devices 216. As such, one manner of providing such uniform pressure/contact may be to individually bias each of the heating devices 216 toward the support plate 203. However, such individual biasing of each heating device 216 may not necessarily be easily accomplished. As such, certain aspects of the present invention contemplate a heating device 216 configured to have an internal biasing mechanism for providing substantially uniform contact/pressure between the heating devices 216 and the corresponding assay devices 118.

FIG. 17 is a side view of one embodiment of an internally-biased heating device 216 implementing a compression spring assembly, which allows a portion (252) of the heating device to yield and contact the assay device 118 at a predetermined pressure, such that the contact/pressure between each of the heating devices 216 and the corresponding assay devices 118 supported by the support plate 203 is substantially the same. Such a heating device 250 may include, for example, a heating element 252 substantially representing the surface of the heating device 216 contacting and transferring heat to a corresponding assay device 118. The heating element 252 is movably engaged with a heater housing 254, and aligned therewith via an alignment element (i.e., a shoulder bolt) 258 engaged therebetween. A compression spring assembly 256 is disposed about the alignment element 258, between the heating element 252 and the heater housing 254, so as to bias the heating element 252 outwardly of the heater housing 254. Since the compression spring assembly 256 may be configured for a particular spring rate, various heating devices 216 configured in a similar manner with compression spring assemblies 256 selected to have the same spring rate may, in some instances, provide substantially the same contact/pressure with adjacent assay devices 118 urged thereagainst (i.e., by suitable placement of the support plate 203). A wiring channel 260 may extend through the heater housing 254 to the heating element 252 so as to allow an electrical conductor (wire) to be directed through the heater housing 254 to the heating element 252 to provide, for example, the necessary voltage for generating resistive heat via the heating element 252.

The manner in which the heating device 216 is internally biased may vary. For example, FIG. 18 is a side view of a heating device 216 implementing a wave spring assembly 272 for biasing the heating element 252, instead of a compression spring assembly. In yet another embodiment of the invention, a heating device 216 may comprise a foam assembly 280 for providing the necessary biasing of the heating element 252, as illustrated in FIG. 19. In yet other embodiments of the invention, the heating device is a pad heater and internal biasing is not necessary. For example, a pad heater can be a silicon pad affixed to a substantially rigid support base.

FIG. 20 is a flowchart, according to one aspect of the invention, showing the steps for preparing an immunocytochemistry assay for a sample in a sample preparation device 100. Processing is started 302 either manually or by the control system 108. Sample tubes are loaded 304 into the sample preparation device 100. The system software for executing the various sequences of the sample preparation device 100 is then started 306. A cell deposition sequence 310 is implemented in order to dispose a sample onto the surface of an assay device, such as a slide 118. The steps of a cell deposition sequence, according to an embodiment of the invention, are shown, for example, in FIG. 21. The sequence is started 312 by retrieving a new tip 316 from the tip cartridge 114. In an embodiment of the invention, where the transfer assembly 110 has a plurality of aspiration and dispensing arms 111, then any or all of the arms may receive a new tip 112 from the tip cartridge 114. The transfer assembly 110 is positioned such that the new tip 112 is aligned with and becomes submerged into the sample of a sample tube 318. The sample, or a sample portion, is withdrawn or aspirated from the sample tube 320. The transfer assembly 110 is positioned such that the tip 112 containing the sample is aligned with a slide 322. The sample is dispensed onto the surface of the slide 324. The transfer assembly 110 is positioned such that the tip 112 is aligned with the tip discard tray 326. The used tip is (or used tips are) released and discarded into the tip discard tray 328. If any samples remain that need to be processed 330 and there are unused slides available 332, then control is returned 314 in order to allow the cell deposition process to continue on the remaining samples. If either no samples remain to be processed 330 or there are no unused slides available to be processed 332, the control system 108 is directed 334 to allow the cell deposition process to terminate 336. Any samples that have not been deposited will be processed when the cell deposition sequence is started in the next processing cycle.

As shown in FIG. 20, after the cell deposition sequence 310 completes, the epitope retrieval sequence 340 begins. FIG. 22 shows the starting of an epitope retrieval process 342 by first applying an epitope retrieval solution to the sample portion that has been disposed onto the slide 346 with such a sample portion being processed according to an immunocytochemistry assay. Processing continues 344 as long as untreated slides requiring epitope retrieval remain 348. In this exemplary embodiment of the invention, the slides may be heated to an elevated temperature 354 and the temperature maintained 356 for a specified heating period 358. In one embodiment of the invention, the elevated temperature is about 95° C. In other embodiments of the invention, the elevated temperature is less than about 95° C. In yet other embodiments of the invention, the slides need not be substantially heated after application of the epitope retrieval solution. Following heating 356, the slides are allowed to cool by exposure to atmosphere at room temperature 360 for a specified cooling period 362. In another embodiment of the invention, the slides are allowed to cool by exposure to atmosphere at room temperature until the slides reach a specified temperature (not shown). Following the cooling step, the slides may be rinsed 364, in some instances, with de-ionized water or some other rinse solution. Indeed, in other embodiments the slides are cooled through the application of the rinse solution. The epitope retrieval sequence is then terminated 366.

Following the epitope retrieval sequence 340 the slides are subjected to a staining sequence 370, which requires the addition of one or more reagents. A heating period may follow each reagent addition step. Any excess of the one or more reagents is removed from the slides. In an exemplary embodiment of a staining procedure, the slides are treated with one or more blocking agents and one or more antibodies, with each deposition being followed by a heating period. Detection reagents are then applied to the cell deposition layer. Detection chemistry may include the steps of detection reagent addition, heating, and removal of excess reagent from the slides. In one instance, detection chemistry includes further preparing the slides to maximize the signal to noise ratio of an antibody. A counterstain reagent may further be added to the slides.

FIG. 23 provides an overview of an exemplary process that employs various procedures as part of the staining process. The staining sequence starts 372 by first applying one or more blocking agents to the slide 374. Following epitope retrieval, samples can be blocked using an appropriate blocking agent. For example, a peroxidase blocking reagent such as hydrogen peroxide may be used as the blocking agent. In other embodiments of the invention, the samples are blocked using a protein blocking reagent to prevent non-specific binding of the epitope antibody. A non-limiting example of a protein blocking reagent is purified casein.

At least one antibody is disposed across the cell deposition layer 376. In one instance, an antibody, particularly a monoclonal antibody, directed to a biomarker of interest is heated with the sample. One of skill in the art will appreciate that a more accurate diagnosis of high-grade cervical disease may be obtained in some cases by detecting more than one biomarker in a patient sample. Therefore, in certain embodiments of the invention, at least two antibodies directed to two distinct biomarkers are used to detect high-grade cervical disease. When more than one antibody is used, these antibodies may be added to a single sample sequentially as individual antibody reagents or simultaneously as an antibody cocktail. In another embodiment of the invention, each individual antibody may be included in the development of a separate assay using a portion of a sample from the same patient, and the resulting data pooled. In another embodiment of the invention, an antibody cocktail comprises at least three antibodies, wherein two antibodies specifically bind to MCM2 and a third antibody specifically binds to Topo2A. Following the application of the antibody(ies), the slides are heated for a desired period of time. Any excess blocking agent is removed from the slides. In one instance, a procedure may be used to remove the excess blocking agent without a need to rinse the slides. A detection chemistry procedure 378 follows the addition of blocking agent(s) and/or antibody(ies). A counterstaining procedure 380 can begin once the detection chemistry procedure is completed 378. After the counterstaining procedure 380 completes, the staining sequence terminates 382. Optionally, a coverslip may be applied to the slide 390 following the staining sequence 370. U.S. Pat. Appl. Publ. No. 2009/0075300 entitled "Methods and Compositions for the Detection of Cervical Cancer" and U.S. Pat. Appl. Publ. No. 2006/0252105 entitled "Monoclonal Antibodies and Methods for Their Use in the Detection of Cervical Cancer" both of which are fully incorporated herein by reference, provide a more detailed description of the compositions and methods for identifying cervical disease in a patient sample.

Many modifications and other embodiments of the invention set forth herein will come to mind to one skilled in the art to which this inventions pertain having the benefit of the teachings presented in the descriptions herein and the associated drawings. Therefore, it is to be understood that the inventions are not to be limited to the specific embodiments disclosed and that modifications and other embodiments are intended to be included within the scope of the appended claims.

That which is claimed:

1. A sample preparation device for preparing a sample according to an assay protocol, comprising:
   a plurality of support devices, each support device configured to support a plurality of assay devices;
   a cell deposition module operably engaged with the support devices and configured to deposit a sample on each of the plurality of assay devices supported by the support devices;
   an epitope retrieval module operably engaged with the support devices and the cell deposition module, and configured to deposit at least one reagent on each of the samples according to the assay protocol;
   a staining module operably engaged with the support devices, the cell deposition module, and the epitope retrieval module, the staining module being configured to deposit a staining reagent on each of the samples according to the assay protocol, and to remove excess staining reagent therefrom upon staining of the samples, the staining module, the epitope retrieval module, and the cell deposition module cooperating with the support devices to form a unitary sample preparation device for preparing the sample without movement of the assay devices via the support devices; and
   a plurality of heating source devices disposed in a heating module assembly on which the support devices are placed, each heating device associated with a support device for heating the samples corresponding to each of the plurality of assay devices to a selected temperature, wherein each heating source device is operably engaged with the associated support device and has a biasing mechanism to bring the heating source device into compliance with the corresponding assay device by the assembly so as to heat each of the plurality of assay devices to the selected temperature, in conjunction with the epitope retrieval module depositing the at least one reagent on each of the samples, according to the assay protocol.

2. A device according to claim 1, wherein the sample is a cytological sample.

3. A device according to claim 2, wherein the assay protocol is an immunocytochemistry assay protocol.

4. A device according to claim 1, wherein the assay device is a slide.

5. A device according to claim 1, further comprising a control system in communication with at least one of the cell deposition module, the epitope retrieval module, and the staining module, the control system being responsive to the assay protocol to automatically control and perform at least one of the sample deposition, the reagent deposition, and the staining reagent deposition and removal.

6. A device according to claim 1, wherein the staining module, the epitope retrieval module, and the cell deposition module cooperate with the support devices and the heating devices to form a unitary sample preparation device for preparing the sample without movement of the assay devices via the support devices.

7. A device according to claim 6, further comprising a control system in communication with at least one of the cell deposition module, the epitope retrieval module, the heating devices, and the staining module, the control system being responsive to the assay protocol to automatically control and perform at least one of the sample deposition, the reagent deposition, the assay device heating, and the staining reagent deposition and removal.

8. A device according to claim 6, wherein the support devices are further configured to support the assay devices in an array having at least one row and at least one column, and wherein each of the cell deposition module, the epitope retrieval module, the heating devices, and the staining module is configured to substantially simultaneously interact with the assay devices disposed in at least one of one of the rows and one of the columns of the array.

9. A device according to claim 6, further comprising an actuating device configured to receive the support devices and to actuate the assay devices into engagement with the heating devices.

* * * * *